(12) United States Patent
Magnani et al.

(10) Patent No.: US 7,361,644 B2
(45) Date of Patent: *Apr. 22, 2008

(54) SPECIFIC ANTAGONIST FOR BOTH E- AND P-SELECTINS

(75) Inventors: John L. Magnani, Gaithersburg, MD (US); John T. Patton, Jr., Gaithersburg, MD (US)

(73) Assignee: Glycomimetics, Inc., Gaithersburg, MD (US)

( * ) Notice: Subject to any disclaimer, the term of this patent is extended or adjusted under 35 U.S.C. 154(b) by 512 days.

This patent is subject to a terminal disclaimer.

(21) Appl. No.: 10/992,480

(22) Filed: Nov. 18, 2004

(65) Prior Publication Data

US 2005/0164982 A1   Jul. 28, 2005

Related U.S. Application Data

(60) Provisional application No. 60/523,775, filed on Nov. 19, 2003, provisional application No. 60/582,435, filed on Jun. 24, 2004.

(51) Int. Cl.
A61K 31/7072 (2006.01)
C08B 37/00 (2006.01)

(52) U.S. Cl. .......................................... 514/54; 536/53
(58) Field of Classification Search ................. 514/54; 536/53
See application file for complete search history.

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | 530/387 |
| 4,859,769 A | 8/1989 | Karlsson et al. | 536/53 |
| 4,876,199 A | 10/1989 | Hakamori | 530/387 |
| 4,925,796 A | 5/1990 | Bergh et al. | 435/97 |
| 4,946,830 A | 8/1990 | Pulverer et al. | 514/23 |
| 5,143,712 A | 9/1992 | Brandley et al. | 424/1.1 |
| 5,151,360 A | 9/1992 | Handa et al. | 435/240.2 |
| 5,211,937 A | 5/1993 | Brandley et al. | 424/1.1 |
| 5,268,364 A | 12/1993 | Kojima et al. | 514/25 |
| 5,304,640 A | 4/1994 | Lasky et al. | 536/23.5 |
| 5,352,670 A | 10/1994 | Venot et al. | 514/54 |
| 5,369,096 A | 11/1994 | Yamada et al. | 514/61 |
| 5,412,123 A | 5/1995 | Rao et al. | 552/290 |
| 5,444,050 A | 8/1995 | Kogan et al. | 514/25 |
| 5,464,778 A | 11/1995 | Cummings et al. | 436/503 |
| 5,464,815 A | 11/1995 | Chamow et al. | 514/8 |
| 5,470,843 A | 11/1995 | Stahl et al. | 514/61 |
| 5,484,891 A | 1/1996 | Lasky et al. | 530/387.3 |
| 5,486,536 A | 1/1996 | Ward et al. | 514/460 |
| 5,519,008 A | 5/1996 | Rao et al. | 514/26 |
| 5,527,785 A | 6/1996 | Bevilacqua et al. | 514/56 |
| 5,538,724 A | 7/1996 | Butcher et al. | 424/152.1 |
| 5,559,103 A | 9/1996 | Gaeta et al. | 514/54 |
| 5,576,305 A | 11/1996 | Ratcliffe | 514/25 |
| 5,580,858 A | 12/1996 | Ippolito et al. | 514/25 |
| 5,580,862 A | 12/1996 | Rosen et al. | 514/61 |
| 5,589,465 A | 12/1996 | Ishida et al. | 514/25 |
| 5,604,207 A | 2/1997 | DeFrees et al. | 514/25 |
| 5,618,785 A | 4/1997 | Heavner et al. | 514/2 |
| 5,622,937 A | 4/1997 | Kogan et al. | 514/25 |
| 5,639,734 A | 6/1997 | Esko et al. | 514/25 |
| 5,646,123 A | 7/1997 | Ippolito et al. | 514/25 |
| 5,646,248 A | 7/1997 | Sawada et al. | 530/350 |
| 5,648,344 A | 7/1997 | Brandley et al. | 514/61 |
| 5,654,282 A | 8/1997 | Tang et al. | 514/25 |
| 5,654,412 A | 8/1997 | Srivastava et al. | 536/18.5 |
| 5,658,880 A | 8/1997 | Dasgupta et al. | 514/8 |
| 5,663,151 A | 9/1997 | Martel et al. | 514/25 |
| 5,679,321 A | 10/1997 | Dasgupta et al. | 424/9.1 |
| 5,679,644 A | 10/1997 | Rao et al. | 514/26 |
| 5,686,426 A | 11/1997 | Martel et al. | 514/25 |
| 5,693,621 A | 12/1997 | Toepfer et al. | 514/25 |
| 5,695,752 A | 12/1997 | Rosen et al. | 424/94.61 |
| 5,710,023 A | 1/1998 | Collins et al. | 435/69.1 |
| 5,710,123 A | 1/1998 | Heavner et al. | 514/2 |
| 5,723,583 A | 3/1998 | Seed et al. | 530/387.3 |
| 5,728,685 A | 3/1998 | Abbas et al. | 514/53 |
| 5,739,300 A | 4/1998 | Toepfer et al. | 536/4.1 |
| 5,747,463 A | 5/1998 | Marinier et al. | 514/25 |
| 5,750,508 A | 5/1998 | Dasgupta et al. | 514/25 |
| 5,753,617 A | 5/1998 | Heavner et al. | 514/9 |

(Continued)

FOREIGN PATENT DOCUMENTS

EP   319 253 A2   6/1989

(Continued)

OTHER PUBLICATIONS

Goodman and Gilman's "The Pharmacological Basis of Therapeutics", 10th Ed., 1996, pp. 54-57.*
Thoma, G. et al., "Preorganization of the Bioactive Conformation of Sialyl Lewis[X] Analogues Correlates with Their Affinity to E-Selectin," *Angew. Chem. Int. Ed.* 40(10):1941-1945, 2001.
Abraham, W.M. et al., "Selectin Blockade Prevents Antigen-induced Late Bronchial Responses and Airway Hyperresponsiveness in Allergic Sheep," *Am J. Respir Crit Care Med.* 159(4): 1205-1214, Apr. 1999.
Baeckström et al., "Purification and Characterization of a Membrane-bound and a Secreted Mucin-type Glycoprotein Carrying the Carcinoma-associated Sialyl-Le[a] Epitope on Distinct Core Proteins," *J. Biol. Chem.* 266(32):21537-21547, Nov. 15, 1991.

(Continued)

*Primary Examiner*—Shaojia Anna Jiang
*Assistant Examiner*—Ganapathy Krishnan
(74) *Attorney, Agent, or Firm*—Seed IP Law Group PLLC

(57) ABSTRACT

Compounds and methods are provided for modulating in vitro and in vivo processes mediated by selectin binding. More specifically, selectin modulators and their use are described, wherein the selectin modulators that modulate (e.g., inhibit or enhance) a selectin-mediated function comprise a particular glycomimetic linked to a particular BASA (Benzyl Amino Sulfonic Acid).

5 Claims, 22 Drawing Sheets

U.S. PATENT DOCUMENTS

| | | | |
|---|---|---|---|
| 5,753,631 A | 5/1998 | Paulson et al. | 514/25 |
| 5,763,413 A | 6/1998 | Numata et al. | 514/25 |
| 5,763,582 A | 6/1998 | Rao et al. | 536/5 |
| 5,789,385 A | 8/1998 | Anderson et al. | 514/25 |
| 5,789,573 A | 8/1998 | Baker et al. | 536/24.5 |
| 5,795,958 A | 8/1998 | Rao et al. | 530/331 |
| 5,811,404 A | 9/1998 | De Frees et al. | 514/25 |
| 5,811,405 A | 9/1998 | Toepfer et al. | 514/25 |
| 5,817,742 A | 10/1998 | Toepfer et al. | 528/328 |
| 5,827,817 A | 10/1998 | Larsen et al. | 514/2 |
| 5,827,837 A | 10/1998 | Bevilacqua et al. | 514/103 |
| 5,830,871 A | 11/1998 | Wong et al. | 514/23 |
| 5,837,689 A | 11/1998 | Anderson et al. | 514/25 |
| 5,837,690 A | 11/1998 | Rao et al. | 514/26 |
| 5,840,679 A | 11/1998 | Larsen et al. | 514/8 |
| 5,854,218 A | 12/1998 | DeFrees | 514/25 |
| 5,858,983 A | 1/1999 | Seed et al. | 514/23 |
| 5,858,994 A | 1/1999 | Kretzschmar et al. | 514/62 |
| 5,880,091 A | 3/1999 | Cummings et al. | 514/8 |
| 5,916,910 A | 6/1999 | Lai | 514/423 |
| 5,919,768 A | 7/1999 | Kogan et al. | 514/25 |
| 5,919,769 A | 7/1999 | Tsukida et al. | 514/25 |
| 5,962,422 A | 10/1999 | Nagy et al. | 514/25 |
| 5,976,540 A | 11/1999 | Rittershaus et al. | 424/184.1 |
| 5,977,080 A | 11/1999 | Rosen et al. | 514/25 |
| 5,985,852 A | 11/1999 | Nagy et al. | 514/54 |
| 5,994,402 A | 11/1999 | Rotstein et al. | 514/547 |
| 6,001,819 A | 12/1999 | Simon et al. | 514/54 |
| 6,001,988 A | 12/1999 | Parma et al. | 536/24.3 |
| 6,033,665 A | 3/2000 | Yednock | 424/130.1 |
| 6,037,333 A | 3/2000 | Panjwani | 514/62 |
| 6,110,897 A | 8/2000 | Unverzagt et al. | 514/25 |
| 6,111,065 A | 8/2000 | Heavner et al. | 530/300 |
| 6,120,751 A | 9/2000 | Unger | 424/9.51 |
| 6,121,233 A | 9/2000 | Magnani et al. | 514/8 |
| 6,124,267 A | 9/2000 | McEver et al. | 514/25 |
| 6,133,239 A | 10/2000 | Handa et al. | 514/25 |
| 6,133,240 A | 10/2000 | Taylor et al. | 514/25 |
| 6,136,790 A | 10/2000 | Toepfer et al. | 514/25 |
| 6,169,077 B1 | 1/2001 | Oehrlein | 514/25 |
| 6,177,547 B1 | 1/2001 | Cummings et al. | 530/388.22 |
| 6,187,754 B1 | 2/2001 | Oehrlein | 514/25 |
| 6,193,973 B1 | 2/2001 | Tuttle | 424/195.1 |
| 6,193,979 B1 | 2/2001 | Rittershaus et al. | 424/195.11 |
| 6,197,752 B1 | 3/2001 | Schmidt et al. | 514/23 |
| 6,225,071 B1 | 5/2001 | Cummings et al. | 435/7.24 |
| 6,235,309 B1 | 5/2001 | Nagy et al. | 424/450 |
| 6,280,932 B1 | 8/2001 | Parma et al. | 435/6 |
| 6,309,639 B1 | 10/2001 | Cummings et al. | 424/143.1 |
| 6,387,884 B1 | 5/2002 | Magnani et al. | 514/25 |
| 6,391,857 B1 | 5/2002 | Magnani et al. | 514/25 |
| 6,407,135 B1 | 6/2002 | Lai et al. | 514/423 |
| 6,465,434 B1 | 10/2002 | Magnani et al. | 514/23 |
| 6,492,332 B1 | 12/2002 | Demopulos et al. | 514/12 |
| 6,503,885 B1 | 1/2003 | Kiso et al. | 514/25 |
| 6,528,487 B1 | 3/2003 | Heavner et al. | 514/13 |
| 7,060,685 B2 * | 6/2006 | Magnani et al. | 514/25 |
| 2001/0046570 A1 | 11/2001 | Nagy et al. | 514/25 |
| 2001/0051370 A1 | 12/2001 | Bistrup et al. | 435/193 |
| 2002/0026033 A1 | 2/2002 | Cummings et al. | 530/322 |
| 2002/0028205 A1 | 3/2002 | Holgersson et al. | 424/184.1 |
| 2002/0031508 A1 | 3/2002 | Wagner et al. | 424/94.63 |
| 2002/0040008 A1 | 4/2002 | Wagner et al. | 514/41 |
| 2002/0132220 A1 | 9/2002 | Berens et al. | 435/1.1 |
| 2002/0164336 A1 | 11/2002 | Harrison et al. | 424/146.1 |
| 2002/0164748 A1 | 11/2002 | Bistrup et al. | 435/193 |
| 2002/0168366 A1 | 11/2002 | Stewart et al. | 424/146.1 |
| 2003/0012787 A1 | 1/2003 | Ashkenazi et al. | 424/145.1 |
| 2003/0012790 A1 | 1/2003 | Ashkenazi et al. | 424/178.1 |
| 2003/0018181 A1 | 1/2003 | Larsen et al. | 536/23.4 |
| 2003/0039683 A1 | 2/2003 | Cantrell et al. | 424/450 |

FOREIGN PATENT DOCUMENTS

| | | |
|---|---|---|
| EP | 381 310 A1 | 8/1990 |
| EP | 408 859 A2 | 1/1991 |
| EP | 671 407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 12/1998 |
| WO | WO 99/42130 | 8/1999 |
| WO | WO 99/43353 | 9/1999 |
| WO | WO 99/43356 | 9/1999 |
| WO | WO 02/22820 | 3/2002 |
| WO | WO 02/062810 | 8/2002 |
| WO | WO 2004/004636 | 1/2004 |
| WO | WO 2004/058304 | 7/2004 |

OTHER PUBLICATIONS

Bänteli, R. et al., "Potent E-Selectin Antagonists," *Helvetica Chimica Acta* 83(11): 2893-2907, 2000.

Berg et al., "A Carbohydrate Domain Common to Both Sialyl Le$^a$ and Sialyl Le$^x$ Is Recognized by the Endothelial Cell Leukocyte Adhesion Molecule ELAM-1," *J. Biol. Chem.* 266(23):14869-14872, Aug. 15, 1991.

Berg et al., "The Cutaneous Lymphocyte Antigen Is a Skin Lymphocyte Homing Receptor for the Vascular Lectin Endothelial Cell-Leukocyte Adhesion Molecule 1," *J. Exp. Med.* 174:1461-1466, Dec. 1991.

Bird and Kimber, "Oligosaccharides Containing Fucose Linked $\alpha(1-3)$ and $\alpha(1-4)$ to N-Acetylglucosamine Cause Decompaction of Mouse Morulae," *Devel. Biol.* 104:449-460, 1984.

Bowen et al., "Characterization of a Human Homologue of the Murine Peripheral Lymph Node Homing Receptor," *Journal of Cell Biology* 109:421-427, Jul. 1989.

Brandley et al., "Carbohydrate Ligands of LEC Cell Adhesion Molecules," *Cell* 63:861-863, Nov. 30, 1990.

Broquet et al., "Effect of Desipramine on a Glycoprotein Sialyltransferase Activity in C6 Cultured Glioma Cells," *J. Neurochem.* 54388:394, 1990.

Childs et al., "High-molecular-weight glycoproteins are the major carriers of the carbohydrate differentiation antigens I, i and SSEA-1 of mouse teratocarcinoma cells," *Biochem. J.* 215:491-503, 1983.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, Nov. 15, 1990.

Datta and Takayama, "Isolation and purification of trehalose 6-mono- and 6,6'-di-corynomycolates from *Corynebacterium matruchotii*. Structural characterization of $^1$H NMR," *Carbohydrate Research* 245: 151-158, 1993.

Duijvestijn et al., "High Endothelial Differentiation in Human Lymphoid and Inflammatory Tissues Defined by Monoclonal Antibody HECA-452," *Am. J. Path.* 130:147-155, Jan. 1988.

Dupré, B. et al., "Glycomimetic Selectin Inhibitors: (α-D-Mannopyranosyloxy)methylbiphenyls," *Bioorganic & Medicinal Chemistry Letters* 6(5):569-572, 1996.

Edgington, "How Sweet It Is: Selectin-Mediating Drugs," *Biotechnology* 10: 383-389, Apr. 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun.* 158(3):913-920, Feb. 15, 1989.

Eggens et al., "Specific Interaction between Le$^X$ and Le$^X$ Determinants. A Possible Basis for Cell Recognition in Preimplantation Embryos and in Embryonal Carcinoma Cells," *J. Biol. Chem.* 264(16):9476-9484, Jun. 5, 1989.

Ernst and Oehrlein, "Substrate and donor specificity of glycosyl transferases," *Glycoconjugate Journal* 16: 161-170, 1999.

Fenderson et al., "A Multivalent Lacto-*N*-Fucopenatose III-Lysyllysine Conjugate Decompacts Preimplantation Mouse Embryos, While the Free Oligosaccharide is Ineffective," *J. Exp. Med.* 160:1591-1596, Nov. 1984.

Fenderson et al., "Coordinate Expression of X and Y Haptens during Murine Embryogenesis," *Devel. Biol.* 114:12-21, 1986.

Fenderson et al., "The blood group I antigen defined by monoclonal antibody C6 is a marker of early mesoderm during murine embryogenesis," *Differentiation* 38:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," *J. Biol. Chem.* 259(7):4681-4685, Apr. 10, 1984.

Fukushi et al., "Novel Fucolipids Accumulating in Human Adenocarcinoma. III. A Hybridoma Antibody (FH6) Defining a Human Cancer-Associated Difucoganglioside (VI$^3$NeuAcV$^3$III$^3$Fuc$_2$nLc$_6$)," *J. Biol. Chem.* 259(16):10511-10517, Aug. 25, 1984.

Gabius et al., "Endogenous Tumor Lectins: Overview and Perspectives," *Anticancer Res.* 6:573-578, 1986.

Gallatin et al., "A cell-surface molecule involved in organ-specific homing of lymphocyctes," *Nature* 304:30-34, Jul. 7, 1983.

Gooi et al., "Stage-specific embryonic antigen involves α 1→3 fucosylated type 2 blood group chains," *Nature* 292:156-158, Jul. 9, 1981.

Hakomori et al., "Novel Fucolipids Accumulating in Human Adenocarcinoma. I. Glycolipids With Di- or Trifucosylated Type 2 Chain," *J. Biol. Chem.* 259(7):4672-4680, Apr. 10, 1984.

Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Comm.* 100(4):1578-1586, Jun. 30, 1981.

Hakomori S., "Aberrant Glycosylation in Cancer Cell Membranes as Focused on Glycolipids: Overview and Perspectives," *Cancer Res.* 45:2405-2414, Jun. 1985.

Handa et al., "Selectin GMP-140 (CD62; PADGEM) Binds to Sialosyl -Le$^a$ and Sialosyl-Le$^X$, and Sulfated Glycans Modulate this Binding," *Biochemical and Biophysical Research Communication* 181(3):1223-1230, Dec. 31, 1991.

Hansson and Zopf, "Biosynthesis of the Cancer-associated Sialyl-Le$^a$ Antigen," *Journal of Biological Chemistry* 260(16):9388-9392, Aug. 5, 1985.

Hasegawa et al., "Synthesis of deoxy-L-fucose-containing sialyl Lewis X ganglioside analogues," *Carbohydrate Research* 257: 67-80, 1994.

Hasegawa et al., "Synthesis of sialyl Lewis X ganglioside analogues containing modified $_L$-fucose residues," *Carbohydrate Research* 274: 165-181, 1995.

Holmes et al., "Enzymatic Basis for the Accumulation of Glycolipids with X and Dimeric X Determinants in Human Lung Cancer Cells (NCI-H69)," *J. Biol. Chem.* 260(12):7619-7627, Jun. 25, 1985.

Huse et al., "Generation of a Large Combinatorial Library of the Immunoglobulin Repertoire in Phage Lambda," *Science* 246:1275-1281, Dec. 8, 1989.

Hynes, R., "Integrins: A Family of Cell Surface Receptors," *Cell* 48:549-554, Feb. 27, 1987.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology* 147:4178-4184, Dec. 15, 1991.

Itai, S. et al., "Differentiation-dependent Expression of I and Sialyl I Antigens in the Developing Lung of Human Embryos and in Lung Cancers," *Cancer Research* 50: 7603-7611, Dec. 1, 1990.

Jeffrey et al., "Affinity Chromatography of Carbohydrate-Specific Immunoglobulins: Coupling of Oligosaccharides to Sepharose ," *Biochem. Biophys. Res. Commun.* 62(3):608-613, 1975.

Jentsch, K.D. et al., "Inhibition of Human Immunodeficiency Virus Type I Reverse Transcriptase by Suramin-related Compounds," *The Journal of General Virology* 68(8): 2183-2192, 1987.

Kannagi et al., "New Globoseries Glycosphingolipids in Human Teratocarcinoma Reactive with the Monoclonal Antibody Directed to a Developmentally Regulated Antigen, State-specific Embryonic Antigen 3," *J. Biol. Chem.* 258(14):8934-8942, Jul. 25, 1983.

Kannagi et al., "State-specific embryonic antigens (SSEA-3 and -4) are epitopes of a unique globo-series ganglioside isolated from human teratocarcinoma cells," *Embo J.* 2(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys.* 11:311-315, 1990.

Kitagawa et al., "Characterization of Mucin-Type Oligosaccharides With the Sialyl-Le$^a$ Structure From Human Colorectal Adenocarcinoma Cells," *Biochem. Biophys. Res. Commun.* 178(3):1429-1436, Aug. 15, 1991.

Kitagawa et al., "Immunoaffinity Isolation of a Sialyl-Le$^a$ Oligosaccharide from Human Milk," *J. Biochem.* 104:591-594, 1988.

Kogan, T.P. et al., "Novel Synthetic Inhibitors of Selectin-Mediated Cell Adhesion: Synthesis of 1,6-Bis[3-(3-carboxymethylphenyl)-4-(2-α-$_D$-mannopyranosyloxy)phenyl]hexane (TBC1269)," *J. Med. Chem* 41:1099-1111, Mar. 26, 1998.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," *J. Med. Chem.* 38: 4976-4984, Dec. 22, 1995.

Kogan, T.P. et al., "Rational Design and Synthesis of Oligosaccharide Mimetics: Selectin Antagonists as Cell Adhesion Inhibitors," *Abstracts of Papers, 210th ACS National Meeting*, American Chemical Society, Chicago, IL, Aug. 20-24, 1995, MEDI-18.

Köhler and Milstein, "Continuous cultures of fused cells secreting antibody of predefined specificity," *Nature* 256:495-497, Aug. 7, 1975.

Köhler and Milstein, "Derivation of specific antibody-producing tissue culture and tumor lines by cell fusion," *Eur. J. Immunol.* 6:511-519, 1976.

Kojima and Hakomori, "Specific Interaction between Gangliotriaosylceramide ($G_{g3}$) and Sialosyllactosylceramide ($G_{M3}$) as a Basis for Specific Cellular Recognition between Lymphoma and Melanoma Cells," *J. Biol. Chem.* 264(34):20159-20162, Dec. 5, 1989.

Koprowski et al., "Colorectal Carcinoma Antigens Detected by Hybridoma Antibodies," *Somatic Cell Genetics* 5(6):957-972, 1979.

Kuzuoka, "Antitumor activity of murine monoclonal antibody NCC-ST-421," *Chem. Ab.* 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed By 500-Mhz H NMR Spectroscopy," *Journal of Biological Chemistry* 259(14):9051-9058, Jul. 25, 1984.

Larsen et al., "PADGEM-Dependent Adhesion of Platelets to Monocytes and Neutrophils Is Mediated by a Lineage-Specific Carbohydrate, LNF III (CD15)," *Cell* 63:467-474, Nov. 2, 1990.

Lindenberg et al., "Carbohydrate binding properties of mouse embryos," *J. Reprod. Fert.* 89:431-439, 1990.

Lipartiti et al., "Monosialoganglioside GM1 Reduces NMDA Neurotoxicity in Neonatal Rat Brain," *Experimental Neurology* 113:301-305, 1991.

Lowe et al., "A transfected human fucosyltransferase CDNA determines biosynthesis of oligosaccharide ligand(s) for endothelial-leukocyte adhesion molecule I," *Biochem. Soc. Trans.* 19(3):649-653, 1991.

Lowe et al., "ELAM-1-Dependent Cell Adhesion to Vascular Endothelium Determined by a Transfected Human Fucosyltransferase cDNA," *Cell* 63:475-484, Nov. 2, 1990.

Macher et al., "A Novel Carbohydrate, Differentiation Antigen on Fucogangliosides of Human Myeloid Cells Recognized by Monoclonal Antibody VIM-2," *Journal of Biological Chemistry* 263(21):10186-10191, Jul. 25, 1988.

Magnani et al., "Identification of the Gastrointestinal and Pancreatic Cancer-associated Antigen Detected by Monoclonal Antibody 19-9 in the Sera of Patients as a Mucin," *Cancer Res.* 43:5489-5492, Nov. 1983.

Magnani et al., "A Monoclonal Antibody-defined Antigen Associated with Gastrointestinal Cancer Is a Ganglioside Containing Sialylated Lacto-N-fucopentaose II," *Journal of Biological Chemistry* 257(23):14365-14369, Dec. 10, 1982.

Magnani, J., "Carbohydrate Sequences Detected By Murine Monoclonal Antibodies," *Chemistry and Physics of Lipids* 42:65-74, 1986.

Mulligan and Berg, "Selection for animal cells that express the *Escherichia coli* gene coding for xanthine-guanine phosphoribosyltransferase," *Proc. Natl. Acad. Sci. USA* 78:2072-2076, Apr. 1981.

Nicolaou et al., "Total Synthesis of the Tumor-Associated Le$^x$ Family of Glycosphingolipids," *J. Amer. Chem. Soc.* 112:3693-3695, 1990.

Nudelman et al., "Novel Fucolipids of Human Adenocarcinoma: Disialosyl Le$^a$ Antigen (III$^4$FucIII$^6$NeuAcIV$^3$NeuAcLc$_4$) of Human Colonic Adenocarcinoma and the Monoclonal Antibody (FH7) Defining This Structure," *J. Biol. Chem.* 261:5487-5495, Apr. 25, 1986.

Orhlein, R., "Carbohydrates and Derivatives as Potential Drug Candidates with Emphasis on the Selectin and Linear-B Area," *Mini Reviews in Medicinal Chemistry* 1: 349-361, 2001.

Palcic et al., "Enzymic Synthesis of Oligosaccharides Terminating in the Tumor-Associated Sialyl-Lewis-a Determinant," *Carbohydr. Res.* 190:1-11, 1989.

Palcic et al., "Regulation of N-Acetylglucosaminyltransferase V Activity. Kinetic Comparisons of Parental, Rous Sarcoma Virus-Transformed BHK, and $_L$-Phytohemagglutinin-Resistand BHK Cells Using Synthetic Substrates and an Inhibitory Substrate Analog," *J. Biol. Chem.* 265:6759-6769, Apr. 25, 1990.

Palcic et al., "A Bisubstrate Analog Inhibitor for $\alpha(1\rightarrow 2)$-Fucosyltransferase," *J. Biol. Chem.* 264:17174-17181, Oct. 15, 1989.

Palma-Vargas, J.M. et al., "Small-Molecule Selectin Inhibitor Protects Against Liver Inflammatory Response After Ischemia and Reperfusion," *J. Am. Coll. Surg.* 185: 365-372, Oct. 1997.

Phillips et al., "ELAM-I Mediates Cell Adhesion by Recognition of a Carbohydrate Ligand, Sialyl-Le$^x$," *Science* 250:1130-1132, Nov. 23, 1990.

Picker et al., "The Neutrophil Selectin LECAM-1 Presents Carbohydrate Ligands to the Vascular Selectins ELAM-I and GMP140," *Cell* 66921-933, Sep. 6, 1991.

Prokazova et al., "Sialylated lactosylceramides. Possible inducers of non-specific immunosuppression and atherosclerotic lesions," *European Journal of Biochemistry* 172:1-6, 1988.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol.* 88:127-137, Jan. 1981.

Rice and Bevilacqua, "An Inducible Endothelial Cell Surface Glycoprotein Mediates Melanoma Adhesion," *Science* 246:1303-1306, Dec. 8, 1989.

Ruoslahti and Pierschbacher, "New Perspectives in Cell Adhesion: RGD and Integrins," *Science* 238:491-497, Oct. 23, 1987.

Sakurai et al., "Selection of a Monoclonal Antibody Reactive with a High-Molecular-Weight Glycoprotein Circulating in the Body Fluid of Gastrointestinal Cancer Patients," *Cancer Research* 48:4053-4058, Jul. 15, 1988.

Sastry et al.,"Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, Aug. 1989.

Scharfman, A. et al., "*Pseudomonas aeruginosa* binds to neoglycoconjugates bearing mucin carbohydrate determinants and predominantly to sialyl-Lewis x conjugates," *Glycobiology* 9(8): 757-764, 1999.

Scharfman, A. et al., "Recognition of Lewis x Derivatives Present on Mucins by Flagellar Components of *Pseudomonas aeruginosa,*" *Infection and Immunity* 69(9): 5243-5248, Sep. 2001.

Shitara et al., "Application of Anti-Sialyl Le$^a$ Monoclonal antibody, KM231, for Immunotherapy of Cancer," *Anticancer Res.* 11:2003-2014, 1991.

Siuzdak et al., "Examination of Sialyl Lewis X—Calcium Complex By Electrospray Mass Spectrometry," *Bioorganic & Medicinal Chemistry Letters* 4(24): 2863-2866, 1994.

Sprengard, U. et al., "Synthesis and Biological Activity of Novel Sialyl-Lewis$^x$ Conjugates," *Bioorganic & Medicinal Chemistry Letters* 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis By One- and Two-Dimensional H NMR Spectroscopy," *J. Biol. Chem.* 263(23):11374-11381, Aug. 15, 1988.

Stephens and Cockett, "The construction of highly efficient and versatile set of mammalian expression vectors," *Nucleic Acids Research.* 17(17):7110, 1989.

Streeter et al., "Immunohistologic and Functional Characterization of a Vascular Addressin Involved in Lymphocyte Homing into Peripheral Lymph Nodes," *Journal of Cell Biology* 107: 1853-1862, Nov. 1988.

Stroud et al., "Extended Type 1 Chain Glycosphingolipids: Dimeric Le$^a$ (III$^4$V$^4$Fuc$_2$Lc$_6$) as Human Tumor-associated Antigen," *J. Biol. Chem.* 266(13):8439-8446, May 5, 1991.

Svenson and Lindberg, "Coupling of Acid Labile *Salmonella* Specific Oligosaccharides to Macromolecular Carriers," *J. Immunol. Meth.* 25:323-335, 1979.

Takada et al., "Adhesion of Human Cancer Cells to Vascular Endothelium Mediated by a Carbohydrate Antigen, Sialyl Lewis A$^1$," *Biochem. Biophys. Res. Commun.* 179(2):713-719, Sep. 16, 1991.

Takeichi, M., "Cadherins: a molecular family essential for selective cell-cell adhesion and animal morphogenesis," *Trends Genet* 3(8):213-217, Aug. 1987.

Thoma, G. et al., "A readily Available, Highly Potent E-Selectin Antagonist," *Angew. Chem. Int. Ed.* 40(19): 3644-3647, 2001.

Thoma, G. et al., "Synthesis and Biological Evaluation of a Sialyl Lewis X Mimic with Significantly Improved E-selectin Inhibition," *Bioorganic & Medicinal Chemistry Letters* 11:923-925, 2001.

Tilton, R.G., "Exdontoxin-Induced Leukocyte Accumulation in Aqueous Fluid of Rats is Decreased by a Small Molecule Selectin," *Investigative Opthalmology & Visual Science* 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA* 79:626-629, Jan. 1982.

Tyrrell et al., "Structural requirements for the carbohydrate ligand of E-selectin," *Proc. Natl. Acad. Sci. USA* 88:10372-10376, Nov. 1991.

Waldmann, H. et al., "Synthesis of 2-Acetamindo-2-Deoxyglucosylasparagine Glyco-Tripeptide and -Pentapeptides By Selective C- and N-Terminal Elongation of the Peptide Chain," *Carbohydrate Research* 196: 75-93, 1990.

Walz et al., "Recognition by ELAM-1 of the Sialyl-Le$^x$ Determinant on Myeloid and Tumor Cells," *Science* 250:1132-1135, Nov. 23, 1990.

Ward and Mulligan, "Blocking of adhesion molecules in vivo as anti-inflammatory therapy," *Immunology* 1: 165-171, 1994.

Whisler and Yates, "Regulation of Lymphocyte Responses By Human Gangliosides. I. Characteristics of Inhibitory Effects and the Induction of Impaired Activation," *Journal of Immunology* 125(5):2106-2111, Nov. 1980.

Yamazaki, F. et al., "Syntheisis of an appropriately protected core glycotetraoside, a key intermediate for the synthesis of 'bisected' complex-type glycans of a glycoprotein," *Carbohydrate Research* *201*: 15-30, 1990.

Zhou et al., "The Selectin GMP-140 Binds to Sialylated, Fucosylated Lactosaminoglycans on Both Myeloid and Nonmyeloid Cells," *Journal of Cell Biology* *115*(2):557-564, Oct. 1991.

Zopf et al., "Affinity Purification of Antibodies Using Oligosaccharide-Phenethylamine Derivatives Coupled to Sepharose," *Meth. Enzymol. 50*:171-175, 1978.

* cited by examiner

Linkage Via Isothiocyanates

BASA-NH₂ + C(=S)Cl₂ ⟶ BASA—N=C=S

BASA—N=C=S + Sugar-NH₂ ⟶ BASA-NH-C(=S)-NH-Sugar

Linkage Via Isocyanates

BASA-NH₂ + C(=O)Cl₂ ⟶ BASA—N=C=O

BASA—N=C=O + Sugar-NH₂ ⟶ BASA-NH-C(=S)-NH-Sugar

Histidine Linker

Linkage through aldehyde

BASA-NH₂ + Sugar-(CH₂)n-CHO ⟶ BASA-NH-CH₂-(CH₂)N-Sugar

Linkage through five carbon spacer Disuccinimidyl Glutarate

SPECIFIC ANTAGONIST FOR BOTH E- AND P-SELECTINS

CROSS-REFERENCES TO RELATED APPLICATIONS

This application claims the benefit of U.S. Provisional Patent Application No. 60/523,775 filed Nov. 19, 2003 and U.S. Provisional Patent Application No. 60/582,435 filed Jun. 24, 2004; where these two provisional applications are incorporated herein by reference in their entireties.

BACKGROUND OF THE INVENTION

1. Field of the Invention

The present invention relates generally to compounds, compositions and methods for modulating processes mediated by selectin binding, and more particularly to selectin modulators and their use, wherein the selectin modulators that modulate a selectin-mediated function comprise a particular glycomimetic linked to a particular BASA (Benzyl Amino Sulfonic Acid).

2. Description of the Related Art

When a tissue is infected or damaged, the inflammatory process directs leukocytes and other immune system components to the site of infection or injury. Within this process, leukocytes play an important role in the engulfment and digestion of microorganisms. Thus, the recruitment of leukocytes to infected or damaged tissue is critical for mounting an effective immune defense.

Selectins are a group of structurally similar cell surface receptors that are important for mediating leukocyte binding to endothelial cells. These proteins are type 1 membrane proteins and are composed of an amino terminal lectin domain, an epidermal growth factor (EGF)-like domain, a variable number of complement receptor related repeats, a hydrophobic domain spanning region and a cytoplasmic domain. The binding interactions appear to be mediated by contact of the lectin domain of the selectins and various carbohydrate ligands.

There are three known selectins: E-selectin, P-selectin and L-selectin. E-selectin is found on the surface of activated endothelial cells, which line the interior wall of capillaries. E-selectin binds to the carbohydrate sialyl-Lewis$^x$ (SLe$^x$), which is presented as a glycoprotein or glycolipid on the surface of certain leukocytes (monocytes and neutrophils) and helps these cells adhere to capillary walls in areas where surrounding tissue is infected or damaged; and E-selectin also binds to sialyl-Lewis$^a$ (SLe$^a$), which is expressed on many tumor cells. P-selectin is expressed on inflamed endothelium and platelets, and also recognizes SLe$^x$ and SLe$^a$, but also contains a second site that interacts with sulfated tyrosine. The expression of E-selectin and P-selectin is generally increased when the tissue adjacent to a capillary is infected or damaged. L selectin is expressed on leukocytes. Selectin-mediated intercellular adhesion is an example of a selectin-mediated function.

Modulators of selectin-mediated function include the PSGL-1 protein (and smaller peptide fragments), fucoidan, glycyrrhizin (and derivatives), anti-selectin antibodies, sulfated lactose derivatives, and heparin. All have shown to be unsuitable for drug development due to insufficient activity, toxicity, lack of specificity, poor ADME characteristics and/or availability of material.

Although selectin-mediated cell adhesion is required for fighting infection and destroying foreign material, there are situations in which such cell adhesion is undesirable or excessive, resulting in tissue damage instead of repair. For example, many pathologies (such as autoimmune and inflammatory diseases, shock and reperfusion injuries) involve abnormal adhesion of white blood cells. Such abnormal cell adhesion may also play a role in transplant and graft rejection. In addition, some circulating cancer cells appear to take advantage of the inflammatory mechanism to bind to activated endothelium. In such circumstances, modulation of selectin-mediated intercellular adhesion may be desirable.

Accordingly, there is a need in the art for identifying inhibitors of selectin-mediated function, e.g., of selectin-dependent cell adhesion, and for the development of methods employing such compounds to inhibit conditions associated with excessive selectin activity. The present invention fulfills these needs and further provides other related advantages.

BRIEF SUMMARY OF THE INVENTION

Briefly stated, this invention provides compounds, compositions and methods for modulating selectin-mediated processes. In the present invention, the compounds that modulate (e.g., inhibit or enhance) a selectin-mediated function contain a particular glycomimetic and a particular BASA (i.e., a benzyl amino sulfonic acid). Such compounds may be combined with a pharmaceutically acceptable carrier or diluent to form a pharmaceutical composition. The compounds or compositions may be used in a method to modulate (e.g., inhibit or enhance) a selectin-mediated function, such as inhibiting a selectin-mediated intercellular adhesion.

In one aspect of the present invention, compounds are provided that contain at least two components: (1) a particular glycomimetic (or glycoconjugate thereof) and (2) a particular BASA. The particular glycomimetic is shown in FIG. 1. The particular BASAs are shown in FIGS. 2 and 5. A compound of the present invention is a combination of a particular glycomimetic and a particular BASA, to yield a compound that modulates (e.g., inhibits or enhances) a selectin-mediated function. The glycomimetic and BASA are covalently linked, for example as shown in FIGS. 3 and 6. Examples of suitable linkers and linkages are shown in FIGS. 3, 6, 8, 11 and 14. An example of a selectin-mediated function is a selectin-mediated intercellular adhesion. A compound of the present invention includes physiologically acceptable salts thereof. A compound of the present invention in combination with a pharmaceutically acceptable carrier or diluent provides a composition of the present invention. A compound or composition of the present invention may further comprise a diagnostic or therapeutic agent.

In the preferred embodiments of the present invention, a compound or physiologically acceptable salt thereof is provided having the formula:

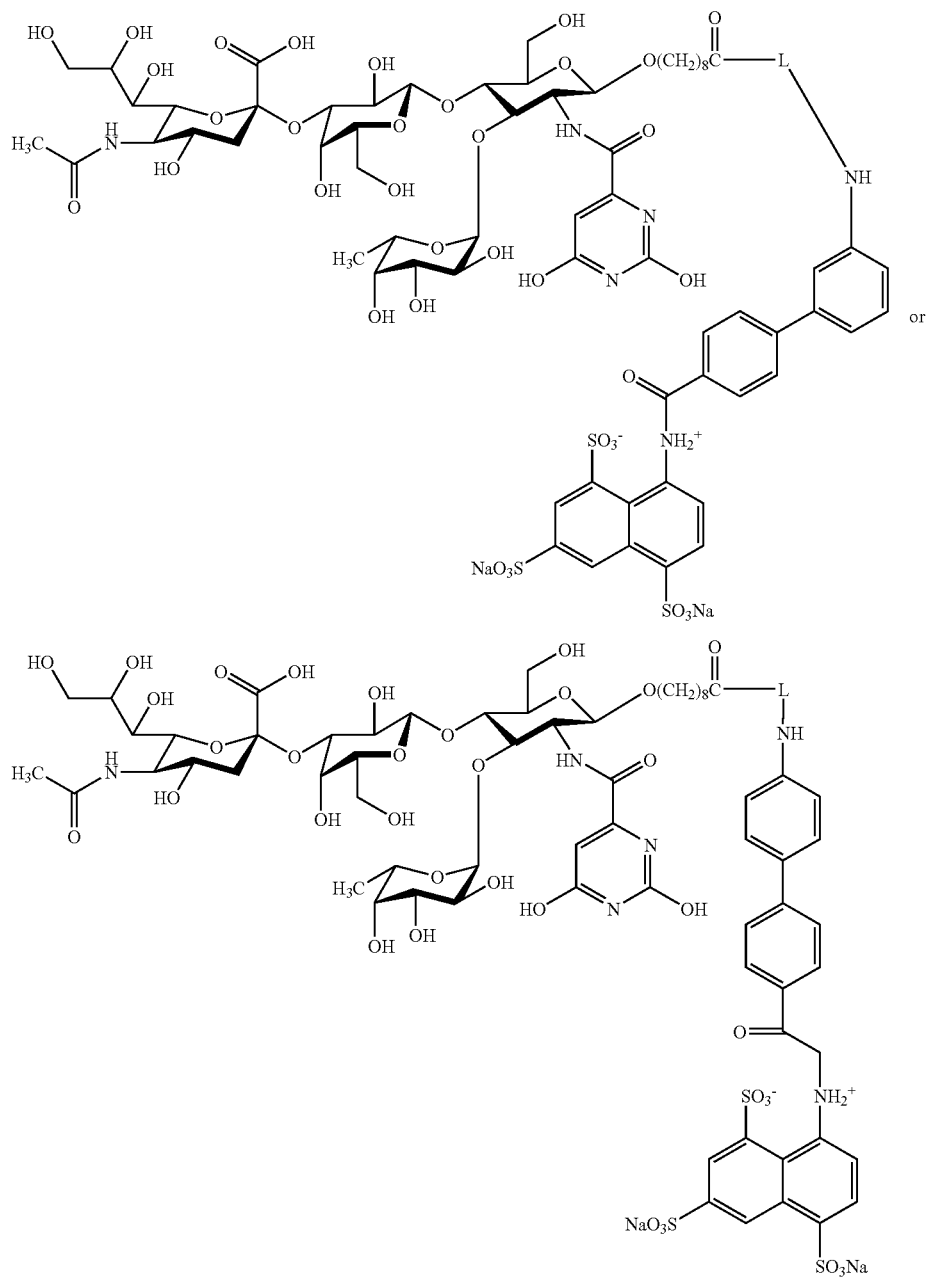
wherein L is a linker. Such a compound may be combined with a pharmaceutically acceptable carrier or diluent to provide a preferred composition of the present invention.
Preferred linkers include where L is
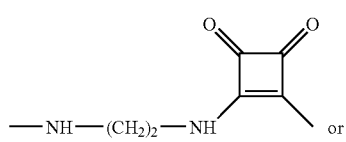
or
-continued
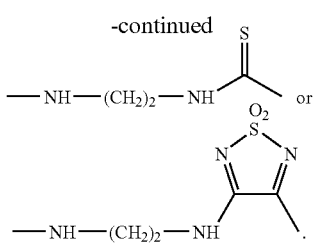

In another aspect of the present invention, methods are provided for using a compound or composition of the present invention to modulate a selectin-mediated function. Such a compound or composition can be used, for example, to inhibit or enhance a selectin-mediated function, such as selectin-mediated intercellular interactions. A compound or composition can be used in a method to contact a cell expressing a selectin in an amount effective to modulate the selectin's function. A compound or composition can be used in a method to administer to a patient, who is in need of having inhibited the development of a condition associated with an excessive selectin-mediated function (such as an excessive selectin-mediated intercellular adhesion), in an amount effective to inhibit the development of such a condition. Examples of such conditions include inflammatory diseases, autoimmune diseases, infection, cancer, shock, thrombosis, wounds, burns, reperfusion injury, platelet-mediated diseases, leukocyte-mediated lung injury, spinal cord damage, digestive tract mucous membrane disorders, osteoporosis, arthritis, asthma and allergic reactions. A compound or composition can be used in a method to administer to a patient who is the recipient of a transplanted tissue in an amount effective to inhibit rejection of the transplanted tissue. A compound or composition can be used in a method in an amount effective to target an agent (e.g., a diagnostic or therapeutic agent) to a selectin-expressing cell by contacting such a cell with the agent linked to the compound or composition. A compound or composition can be used in the manufacture of a medicament, for example for any of the uses recited above.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWING(S)

Figure 14:
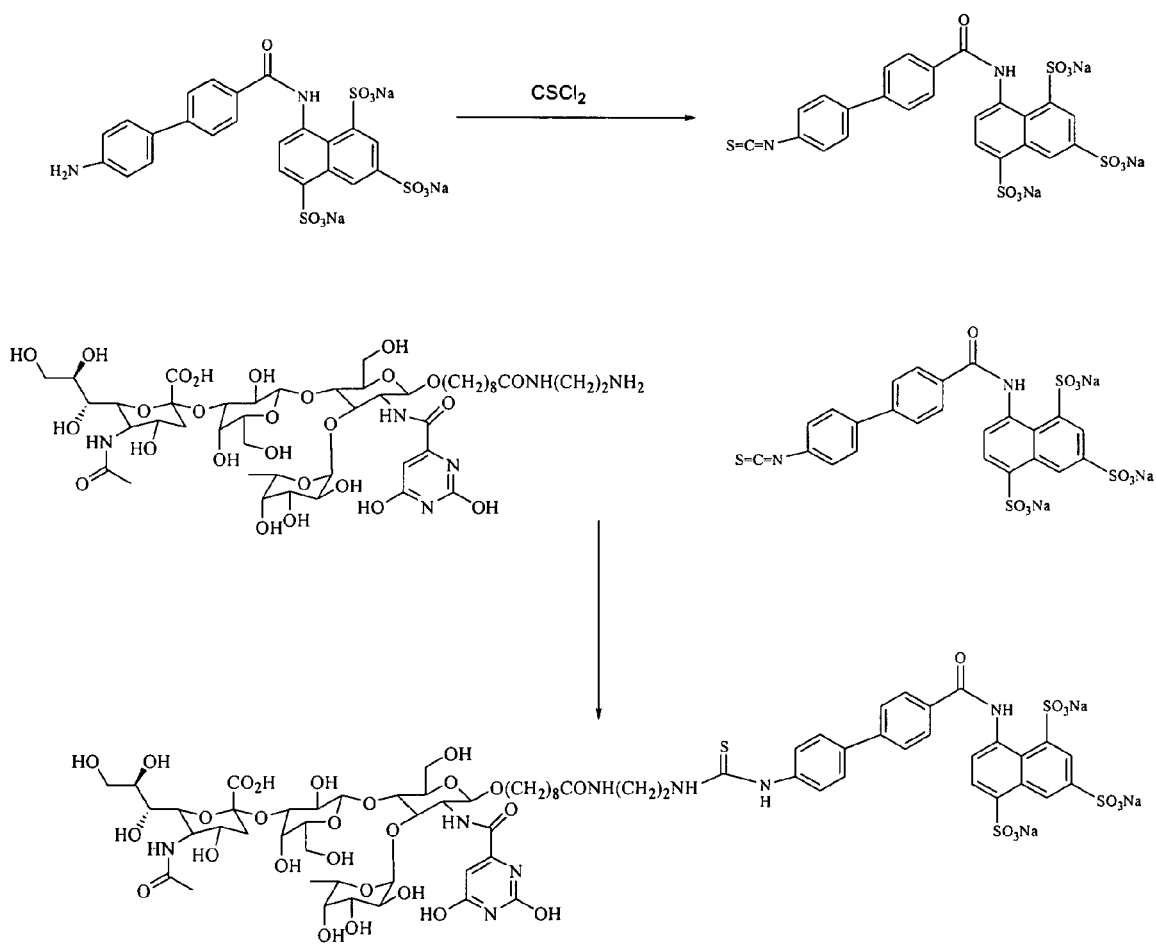
FIG. 14 is a diagram illustrating the synthesis of a glycomimetic linked to a BASA.
Figure 15A:
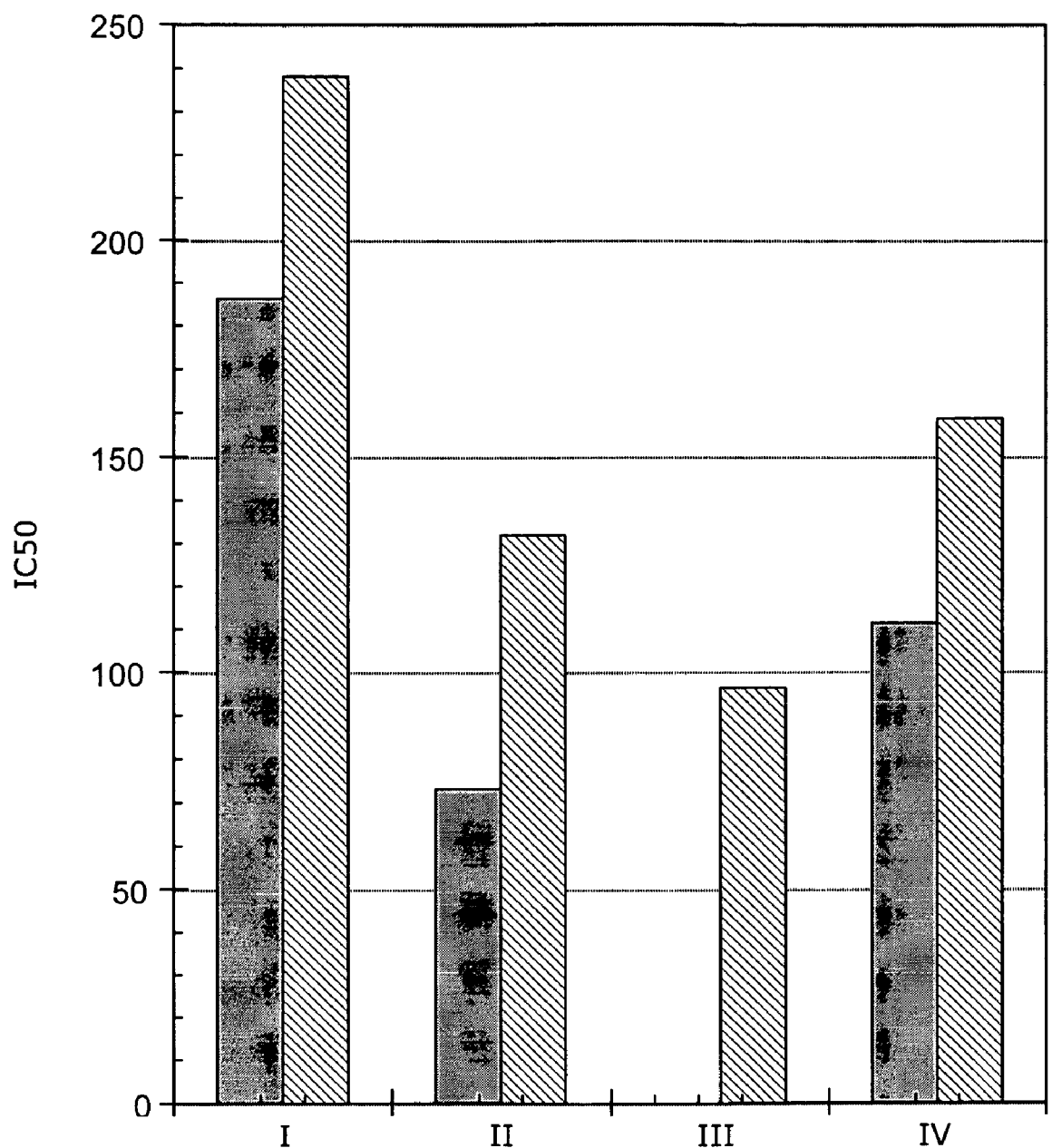
Figure 15B:
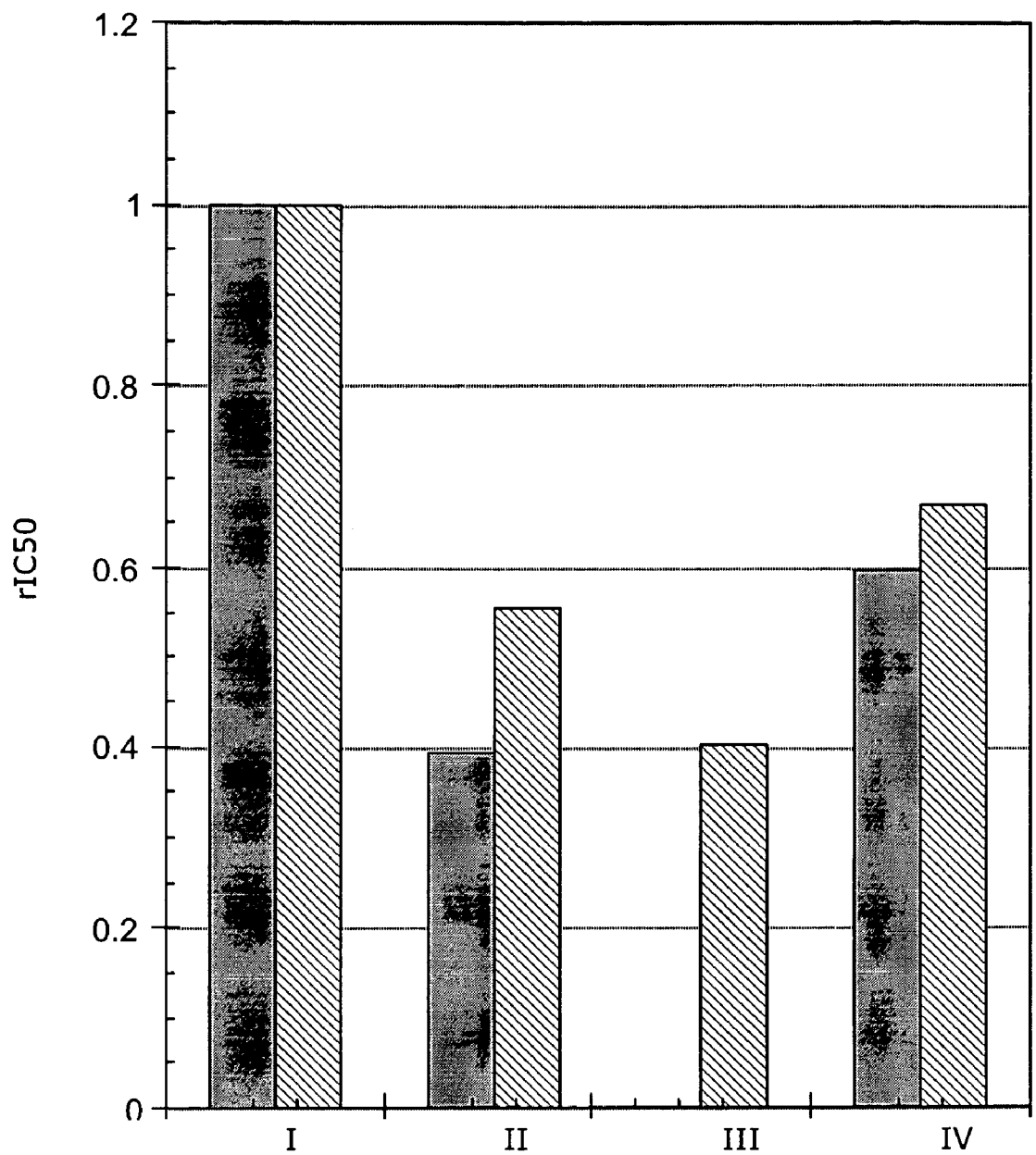

FIGS. 15A-15B show the results of an E-selectin binding assay. FIG. 15A is the raw data for half inhibitory concentration (IC50) and FIG. 15B is the relative half inhibitory concentration (rIC50) where the data for the internal positive control are set to 1.0. The solid and hatched bars represent assays conducted on different days. "I" is an internal positive control compound (compound 15 of Thoma et al., *J. Med. Chem.* 42: 4909-4913, 1999). "II" is the glycomimetic of FIG. 1. "III" is the glycomimetic-BASA of FIG. 13. "IV" is the glycomimetic-BASA of FIG. 14.

Figure 16A:
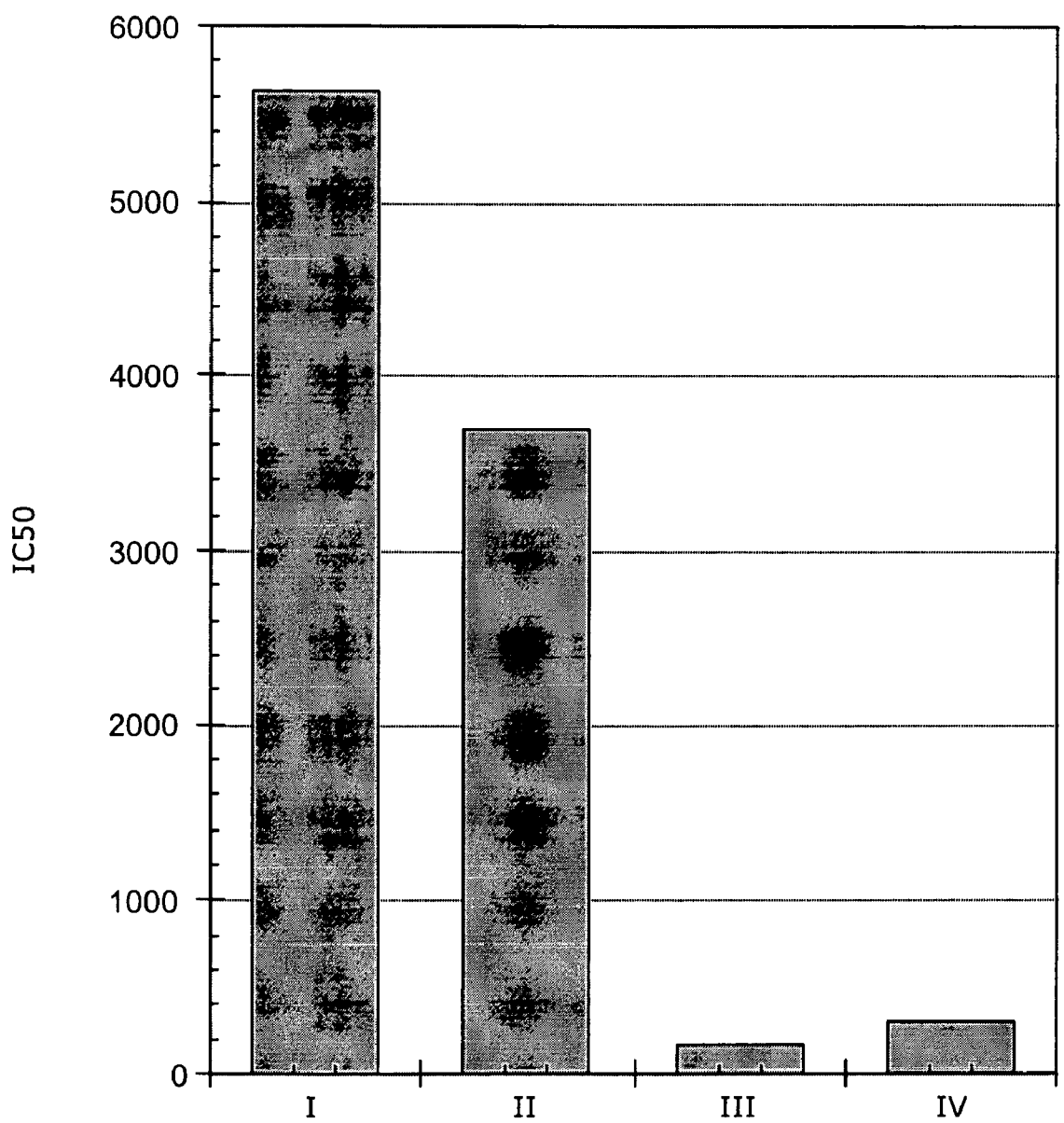
Figure 16B:
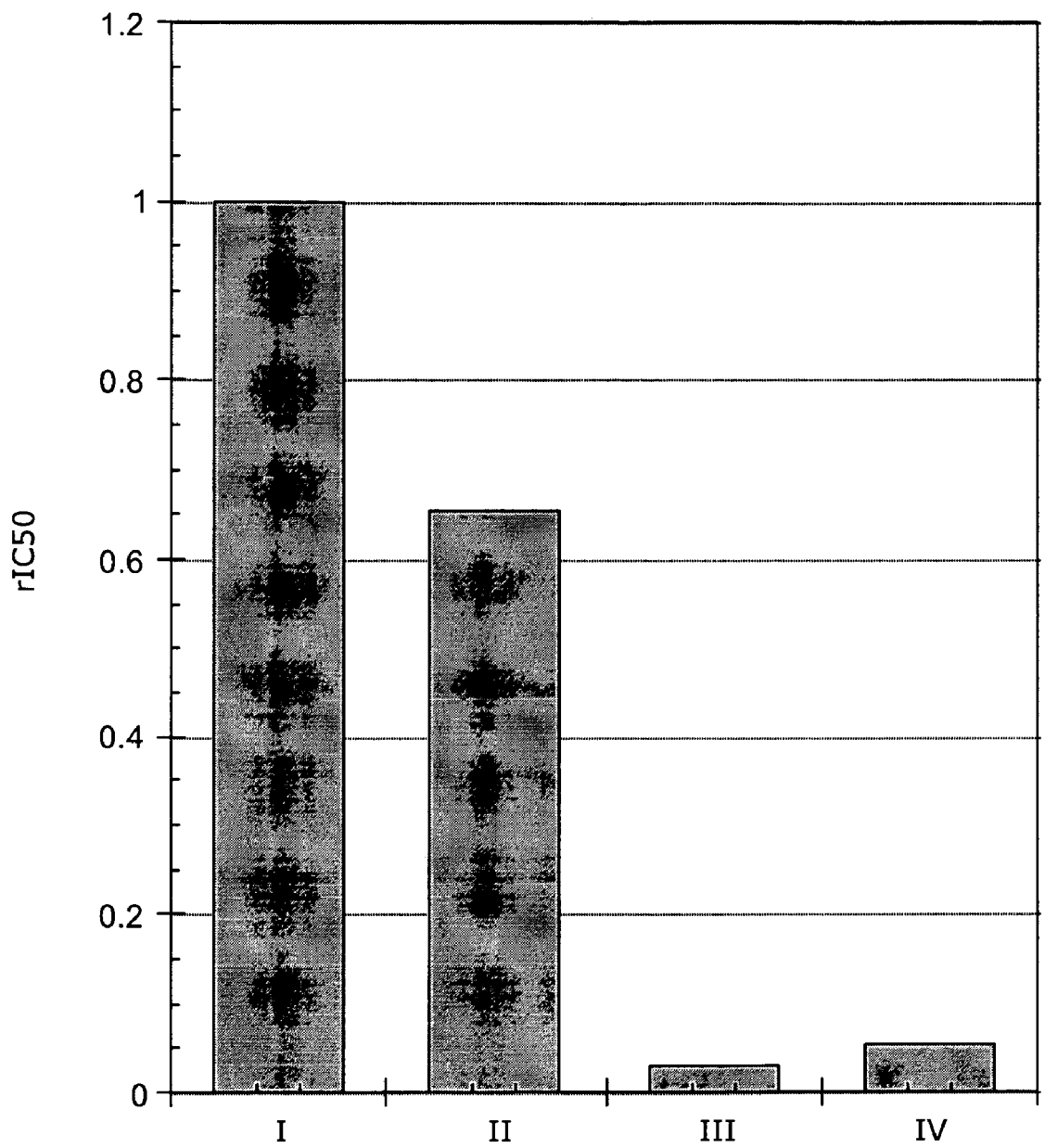

FIGS. 16A-16B show the results of an P-selectin binding assay. FIG. 16A is the raw data for half inhibitory concentration (IC50) and FIG. 16B is the relative half inhibitory concentration (rIC50) where the data for the internal positive control are set to 1.0. "I" is an internal positive control compound (glycyrrhizin). "II" is the glycomimetic of FIG. 1. "III" is the glycomimetic-BASA of FIG. 13. "IV" is the glycomimetic-BASA of FIG. 14.

Figure 6:
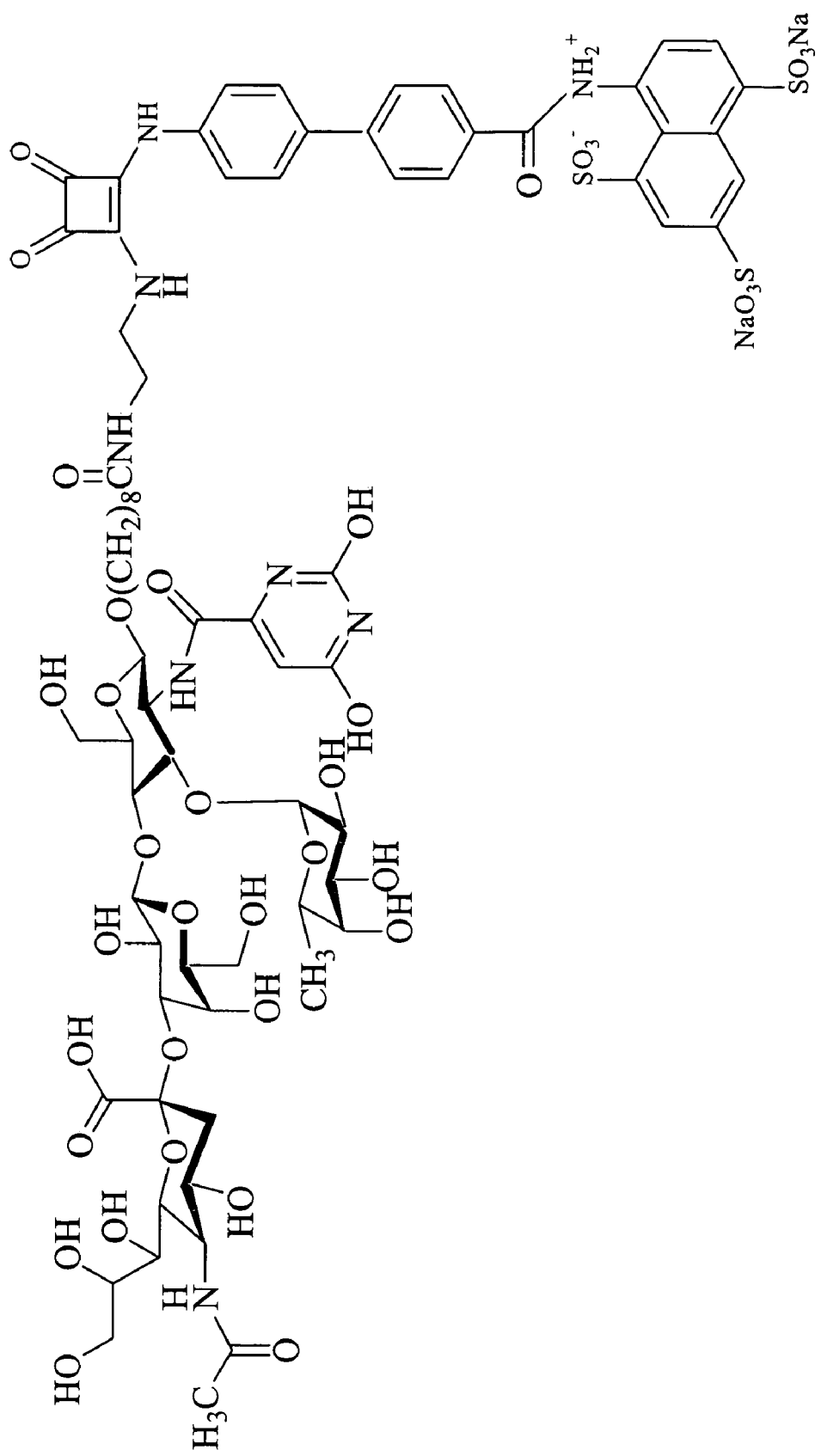
FIG. 6 shows the structure of the glycomimetic of FIG. 1 joined to the BASA of FIG. 5 by a preferred linker.
Figure 7:
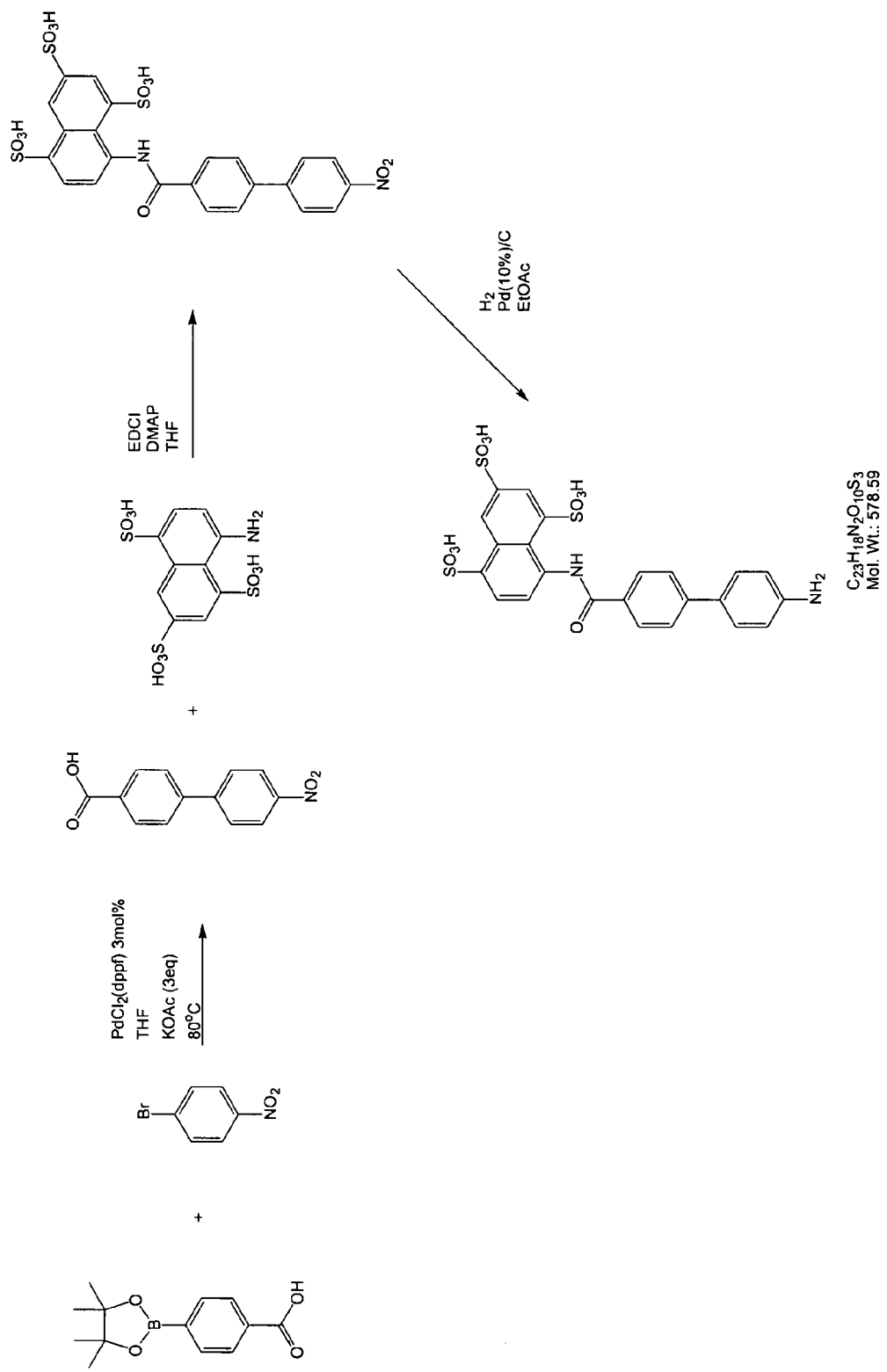
FIG. 7 is a diagram illustrating the synthesis of the BASA of FIG. 5.
Figure 17:
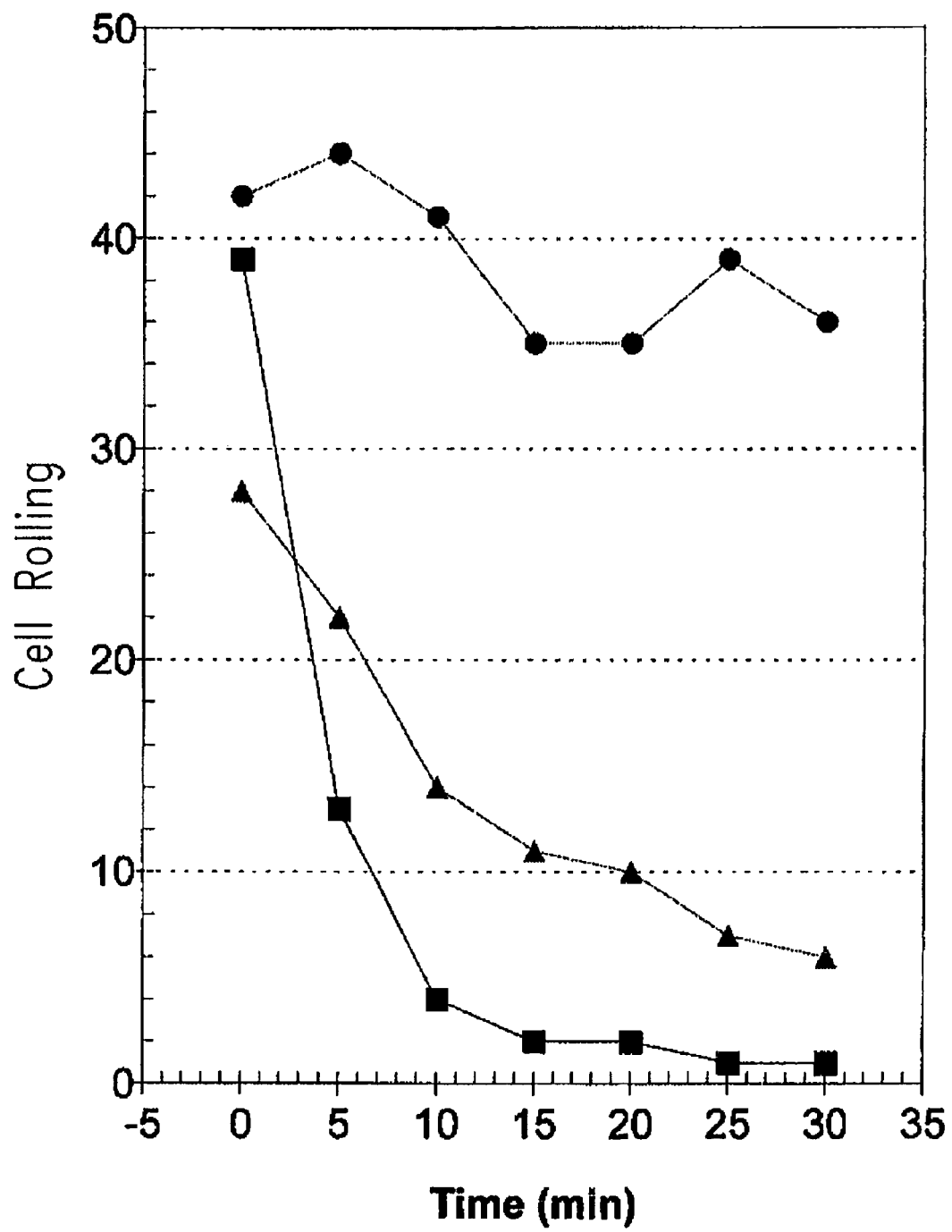

FIG. 17 shows the effect of the selectin modulator of FIG. 6 on cell rolling in established inflammation by intravital microscopy (●vehicle; ■mAbs(3); ▲compound of FIG. 6).

DETAILED DESCRIPTION OF THE INVENTION

As noted above, the present invention provides selectin modulators, compositions thereof and methods for modulating selectin-mediated functions. Such modulators may be used in vitro or in vivo, to modulate (e.g., inhibit or enhance) selectin-mediated functions in a variety of contexts, discussed in further detail below. Examples of selectin-mediated functions include intercellular adhesion and the formation of new capillaries during angiogenesis.

Selectin Modulators

The term "selectin modulator," as used herein, refers to a molecule(s) that modulates (e.g., inhibits or enhances) a selectin-mediated function, such as selectin-mediated intercellular interactions, and that comprises a particular BASA linked to a particular selectin-binding glycomimetic (or glycoconjugate thereof).

A selectin modulator may consist entirely of a particular BASA linked to a particular glycomimetic as described herein, or may comprise one or more additional molecular components. The selectin modulators of the present invention are, surprisingly, significantly more potent than the individual components alone or additively.

A particular BASA is linked (e.g., covalently attached with or without a spacer group) via "L" to a particular selectin-binding glycomimetic (or glycoconjugate thereof) to form a selectin modulator of the present invention. The preferred linkers are shown in FIGS. 3, 6, 11 and 14.

The attachment of a particular BASA to a particular glycomimetic can be accomplished in a variety of ways to form a selectin modulator. A linker "L" possessed by (or added to) either a BASA or a glycomimetic or both may include a spacer group, such as —$(CH_2)_n$— or —O$(CH_2)_n$— where n is generally about 1-20. The simplest attachment method is reductive amination of the BASA to a glycomimetic containing a reducing end (an anomeric hydroxyl/aldehyde). This is accomplished by simple reaction of the BASA to the reducing end and subsequent reduction (e.g., with NaCNBH$_3$) of the imine formed. The most general approach entails the simple attachment of an activated linker to the glycomimetic via an O, S or N heteroatom (or C atom) at the anomeric position. The methodology of such attachments has been extensively researched for carbohydrates and anomeric selectivity is easily accomplished by proper selection of methodology and/or protecting groups. Examples of potential glycosidic synthetic methods include Lewis acid catalyzed bond formation with halogen or peracetylated sugars (Koenigs Knorr), trichloroacetamidate bond formation, thioglycoside activation and coupling, glucal activation and coupling, n-pentenyl coupling, phosphonate ester homologation (Horner-Wadsworth-Emmons reaction), and many others. Alternatively, linkers could be attached to positions on the moieties other than the anomeric. The most accessible site for attachment is at a six hydroxyl (6-OH) position of a glycomimetic (a primary alcohol). The attachment of a linker at the 6-OH can be easily achieved by a variety of means. Examples include reaction of the oxy-anion (alcohol anion formed by deprotonation with base) with an appropriate electrophile such as an alkyl/acyl bromide, chloride or sulfonate ester, activation of the alcohol via reaction with a sulfonate ester chloride or POCl$_3$ and displacement with a subsequent nucleophile, oxidation of the alcohol to the aldehyde or carboxylic acid for coupling, or even use of the Mitsunobu reaction to introduce differing functionalities. Once attached the linker is then functionalized for reaction with a suitable nucleophile on the BASA (or vice versa). This is often accomplished by use of thiophosgene and amines to make thiourea-linked heterobifunctional ligands, diethyl squarate attachment (again with amines) and/or simple alkyl/acylation reactions. Additional methods that could be utilized include FMOC solid or solution phase synthetic techniques traditionally used for carbohydrate and peptide coupling and chemo-enzymatic synthesis techniques possibly utilizing glycosyl/fucosyl transferases and/or oligosaccharyltransferase (OST).

Embodiments of linkers are described in the Examples and also include the following:

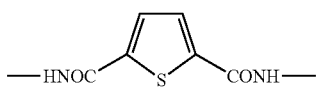

Acylation via Thiofuran

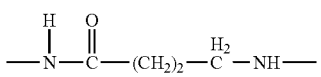

N-Pentenoylation and Reductive Amination

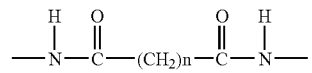

Coupling Via Bifunctional NHS Reagent

Figure 8:
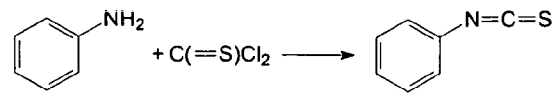
FIG. 8 shows additional preferred linkers and linkages.
Figure 8:
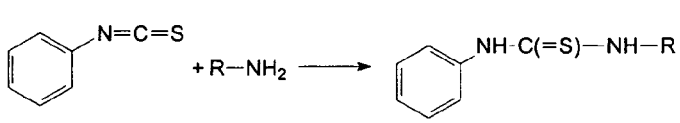
Figure 8:
Figure 8:
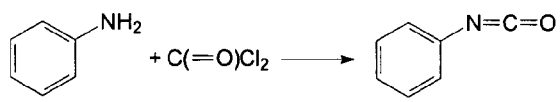
Figure 8:
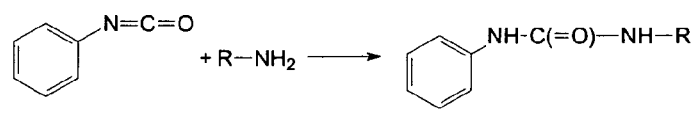
Figure 8:
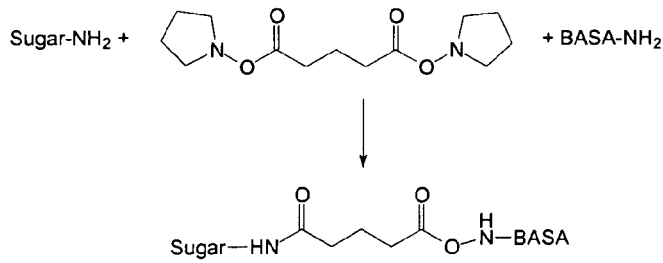

In addition, FIG. 8 shows additional linkers and linkages. Other linkers will be familiar to those in the art.

Although selectin modulators as described herein may sufficiently target a desired site in vivo, it may be beneficial for certain applications to include an additional targeting moiety to facilitate targeting to one or more specific tissues. As used herein, a "targeting moiety," may be any substance (such as a compound or cell) that, when linked to a modulating agent enhances the transport of the modulator to a target tissue, thereby increasing the local concentration of the modulator. Targeting moieties include antibodies or fragments thereof, receptors, ligands and other molecules that bind to cells of, or in the vicinity of, the target tissue. Linkage is generally covalent and may be achieved by, for example, direct condensation or other reactions, or by way of bi- or multi-functional linkers.

For certain embodiments, it may be beneficial to also, or alternatively, link a drug to a selectin modulator. As used herein, the term "drug" refers to any bioactive agent intended for administration to a mammal to prevent or treat a disease or other undesirable condition. Drugs include hormones, growth factors, proteins, peptides and other compounds. Examples of potential drugs include antineoplastic agents (such as 5-fluorouracil and distamycin), integrin agonist/antagonists (such as cyclic-RGD peptide), cytokine agonist/antagonists, histamine agonist/antagonists (such as diphenhydramine and chlorpheniramine), antibiotics (such as aminoglycosides and cephalosporins) and redox active biological agents (such as glutathione and thioredoxin). In other embodiments, diagnostic or therapeutic radionuclides may be linked to a selectin modulator. In many embodiments, the agent may be linked directly or indirectly to a selectin modulator.

Evaluating Inhibition of Selectin-Mediated Intercellular Adhesion

Modulating agents as described above are capable, for example, of inhibiting selectin-mediated cell adhesion. This ability may generally be evaluated using any of a variety of in vitro assays designed to measure the effect on adhesion between selectin-expressing cells (e.g., adhesion between leukocytes or tumor cells and platelets or endothelial cells). For example, such cells may be plated under standard conditions that, in the absence of modulator, permit cell adhesion. In general, a modulator is an inhibitor of selectin-mediated cell adhesion if contact of the test cells with the modulator results in a discernible inhibition of cell adhesion. For example, in the presence of modulators (e.g., micromolar levels), disruption of adhesion between leukocytes or tumor cells and platelets or endothelial cells may be determined visually within approximately several minutes, by observing the reduction of cells interacting with one another.

Selectin Modulator Formulations

Modulators as described herein may be present within a pharmaceutical composition. A pharmaceutical composition comprises one or more modulators in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

A pharmaceutical composition may also, or alternatively, contain one or more active agents, such as drugs (e.g., those set forth above), which may be linked to a modulator or may be free within the composition.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Selectin modulators are generally present within a pharmaceutical composition in a therapeutically effective amount. A therapeutically effective amount is an amount that results in a discernible patient benefit, such as increased healing of a condition associated with excess selectin-mediated function (e.g., intercellular adhesion), as described below.

Selectin Modulator Methods of Use

In general, the modulating agents and compositions described herein may be used for enhancing or inhibiting a selectin-mediated function. Such enhancement or inhibition may be achieved in vitro and/or in vivo in a warm-blooded animal, preferably in a mammal such as a human, provided that a selectin-expressing cell is ultimately contacted with a modulator, in an amount and for a time sufficient to enhance or inhibit selectin-mediated function.

Within certain aspects, the present invention provides methods for inhibiting the development of a condition associated with a selectin-mediated function, such as intercellular adhesion. In general, such methods may be used to prevent, delay or treat such a condition. In other words, therapeutic methods provided herein may be used to treat a disease, or may be used to prevent or delay the onset of such a disease in a patient who is free of disease or who is afflicted with a disease that is not associated with a selectin-mediated function. For example, the therapeutic methods have uses that may include the arrest of cell growth, the killing of cells, the prevention of cells or cell growth, the delay of the onset of cells or cell growth, or the prolongation of survival of an organism.

A variety of conditions are associated with a selectin-mediated function. Such conditions include, for example, tissue transplant rejection, platelet-mediated diseases (e.g., atherosclerosis and clotting), hyperactive coronary circulation, acute leukocyte-mediated lung injury (e.g., adult respiratory distress syndrome (ARDS)), Crohn's disease, inflammatory diseases (e.g., inflammatory bowel disease), autoimmune diseases (MS, myasthenia gravis), infection, cancer (and metastasis), thrombosis, wounds (and wound-associated sepsis), burns, spinal cord damage, digestive tract mucous membrane disorders (gastritis, ulcers), osteoporosis, rheumatoid arthritis, osteoarthritis, asthma, allergy, psoriasis, septic shock, traumatic shock, stroke, nephritis, atopic dermatitis, frostbite injury, adult dyspnoea syndrome, ulcerative colitis, systemic lupus erythematosus, diabetes and reperfusion injury following ischaemic episodes. Selectin modulators may also be administered to a patient prior to heart surgery to enhance recovery. Other uses include pain management, prevention of restinosis associated with vascular stenting, and for undesirable angiogenesis, e.g., associated with cancer.

Selectin modulators of the present invention may be administered in a manner appropriate to the disease to be treated (or prevented). Appropriate dosages and a suitable duration and frequency of administration may be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a selectin modulator may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Selectin modulators may also be used to target substances to cells that express a selectin. Such substances include therapeutic agents and diagnostic agents. Therapeutic agents may be a molecule, virus, viral component, cell, cell component or any other substance that can be demonstrated to modify the properties of a target cell so as to provide a benefit for treating or preventing a disorder or regulating the physiology of a patient. A therapeutic agent may also be a prodrug that generates an agent having a biological activity in vivo. Molecules that may be therapeutic agents may be, for example, polypeptides, amino acids, nucleic acids, polynucleotides, steroids, polysaccharides or inorganic compounds. Such molecules may function in any of a variety of ways, including as enzymes, enzyme inhibitors, hormones, receptors, antisense oligonucleotides, catalytic polynucleotides, anti-viral agents, anti-tumor agents, anti-bacterial agents, immunomodulating agents and cytotoxic agents (e.g., radionuclides such as iodine, bromine, lead, palladium or copper). Diagnostic agents include imaging agents such as metals and radioactive agents (e.g., gallium, technetium, indium, strontium, iodine, barium, bromine and phosphorus-containing compounds), contrast agents, dyes (e.g., fluorescent dyes and chromophores) and enzymes that catalyze a calorimetric or fluorometric reaction. In general, therapeutic and diagnostic agents may be attached to a selectin modulator using a variety of techniques such as those described above. For targeting purposes, a selectin modulator may be administered to a patient as described herein. Since selectins are expressed on endothelial cells involved in the formation of new capillaries during angiogenesis, a selectin modulator may be used to target a therapeutic agent for killing a tumor's vasculature. A selectin modulator may also be used for gene targeting.

Selectin modulators may also be used in vitro, e.g., within a variety of well known cell culture and cell separation methods. For example, modulators may be linked to the interior surface of a tissue culture plate or other cell culture support, for use in immobilizing selectin-expressing cells for screens, assays and growth in culture. Such linkage may be performed by any suitable technique, such as the methods described above, as well as other standard techniques. Modulators may also be used, for example, to facilitate cell identification and sorting in vitro, permitting the selection of cells expressing a selectin (or different selectin levels). Preferably, the modulator(s) for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulator linked to a fluorescent marker, such as fluorescein, is contacted with the cells, which are then analyzed by fluorescence activated cell sorting (FACS).

All compounds of the present invention or useful thereto, include physiologically acceptable salts thereof.

The following Examples are offered by way of illustration and not by way of limitation.

EXAMPLES

Example 1

Figure 4:
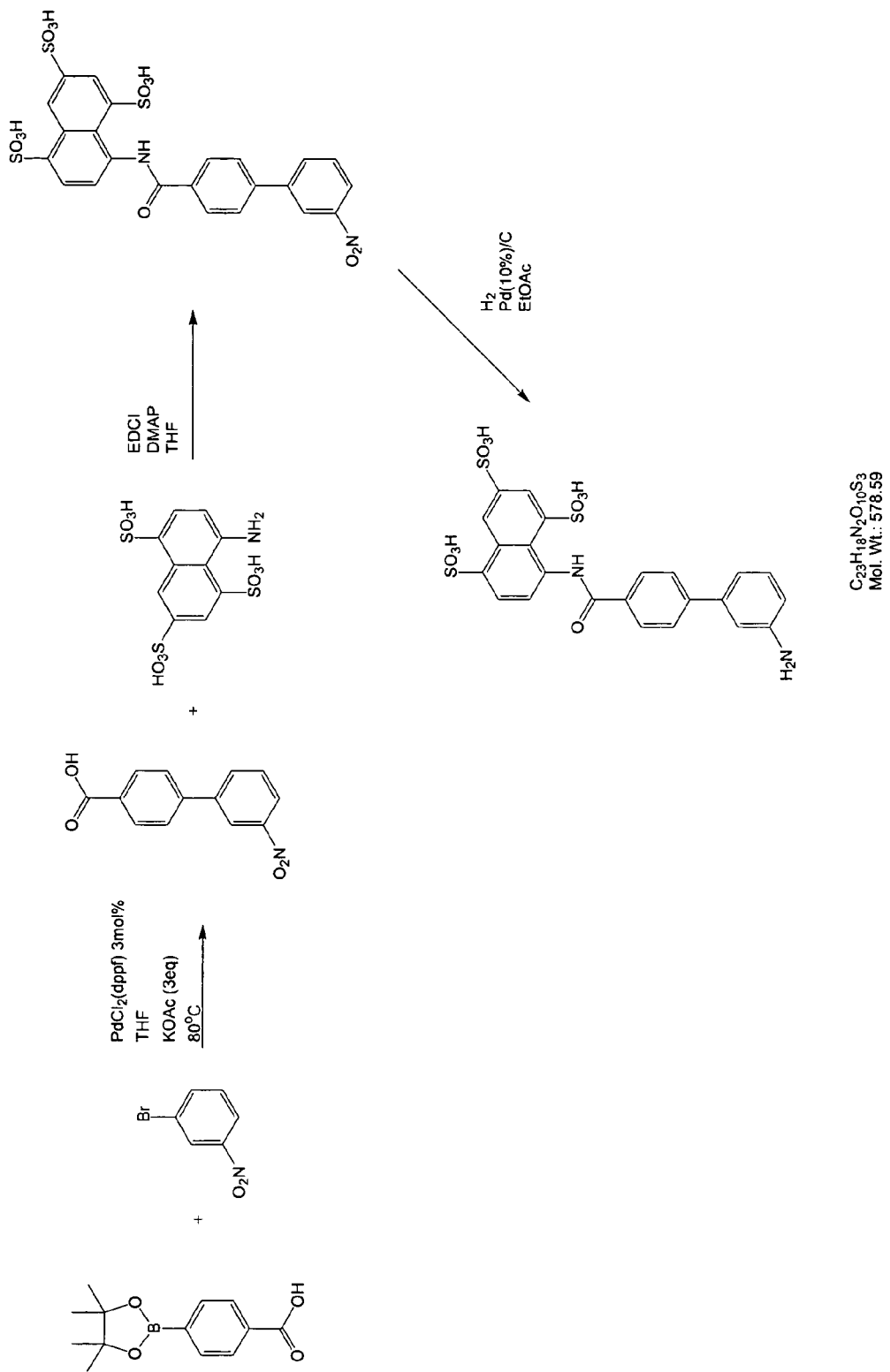
FIG. 4 is a diagram illustrating the synthesis of the BASA of FIG. 2.
Figure 5:
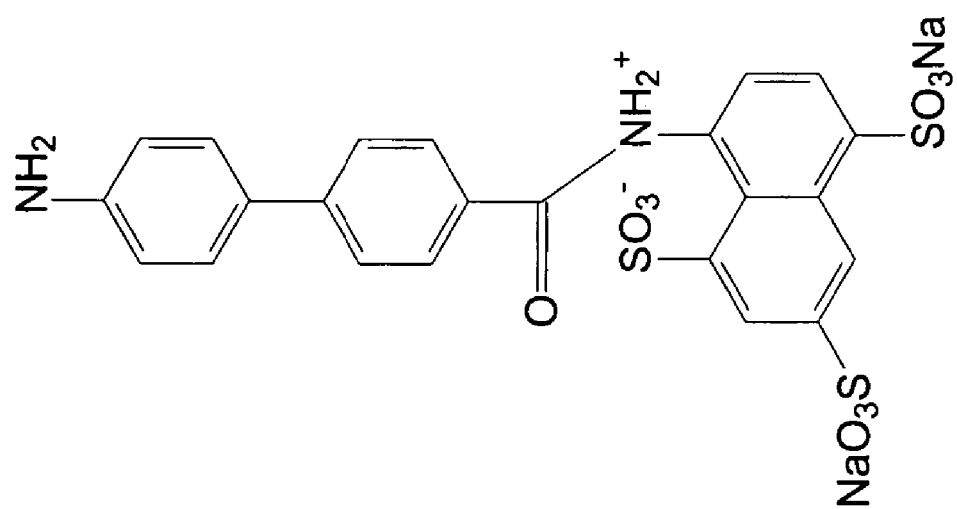
FIG. 5 shows the structure of a particular BASA.

Preparation of a BASA (FIG. 4)

Suzuki Coupling 4-(4,4,5,5-Tetramethyl-[1,3,2]dioxaborolan-2-yl)-benzoic acid (0.004 mol, 1 eq) and KOAc (0.012 mol, 3 eq) are placed in THF (25 ml) creating a slurry. $PdCl_2(dppf)$ (0.00012 mol, 3 mol %) and p-bromo-nitrobenzene (0.005 mol, 1.2 eq) are then added to the solution with stirring and the solution is heated gently to 80° C. After 6 hrs the reaction is complete by TLC (20:1 $CH_2Cl_2/CH_3OH$). The reaction mixture is evaporated to dryness, dissolved in $CH_2Cl_2$ (30 ml) and washed with distilled water and saturated $NaHCO_3$. The resultant biphenyl compound is taken directly to the next step.

Carbodiimide Coupling

4'-Nitro-biphenyl-4-carboxylic acid (0.004 mol, 1 eq), dimethyl amino pyridine (1 crystal, cat.) and EDCI (0.0041 mol, 1.05 eq) are dissolved in DMF (or THF, 20 ml) and allowed to react at room temperature for 10 min. 8-Amino-naphthalene-1,3,5-trisulfonic acid is added to the reaction mixture with stirring and the reaction is allowed to proceed at room temperature under nitrogen for 48 hrs. The reaction mixture is then evaporated to dryness and purified by reverse phase chromatography (C18 column, 80/20 $CH_3CN/H_2O$-1% TFA to 50/50 $CH_3CN/H_2O$).

Hydrogenation

8-[(4'-Nitro-biphenyl-4-carbonyl)-amino]-naphthalene-1,3,5-trisulfonic acid (1 eq) and 10% Pd (10 mol %) on carbon are placed in EtOAc (or $CH_3OH$). The solution is degassed and an atmosphere of $H_2$ is generated within the reaction vessel. The reaction is allowed to proceed until the uptake of $H_2$ ceases and TLC indicates the disappearance of starting material (~12 hrs). The palladium precipitate is removed by filtration through a bed of celite and the filtrate is evaporated to dryness giving the BASA compound of FIG. 4.

Example 2

Figure 9:
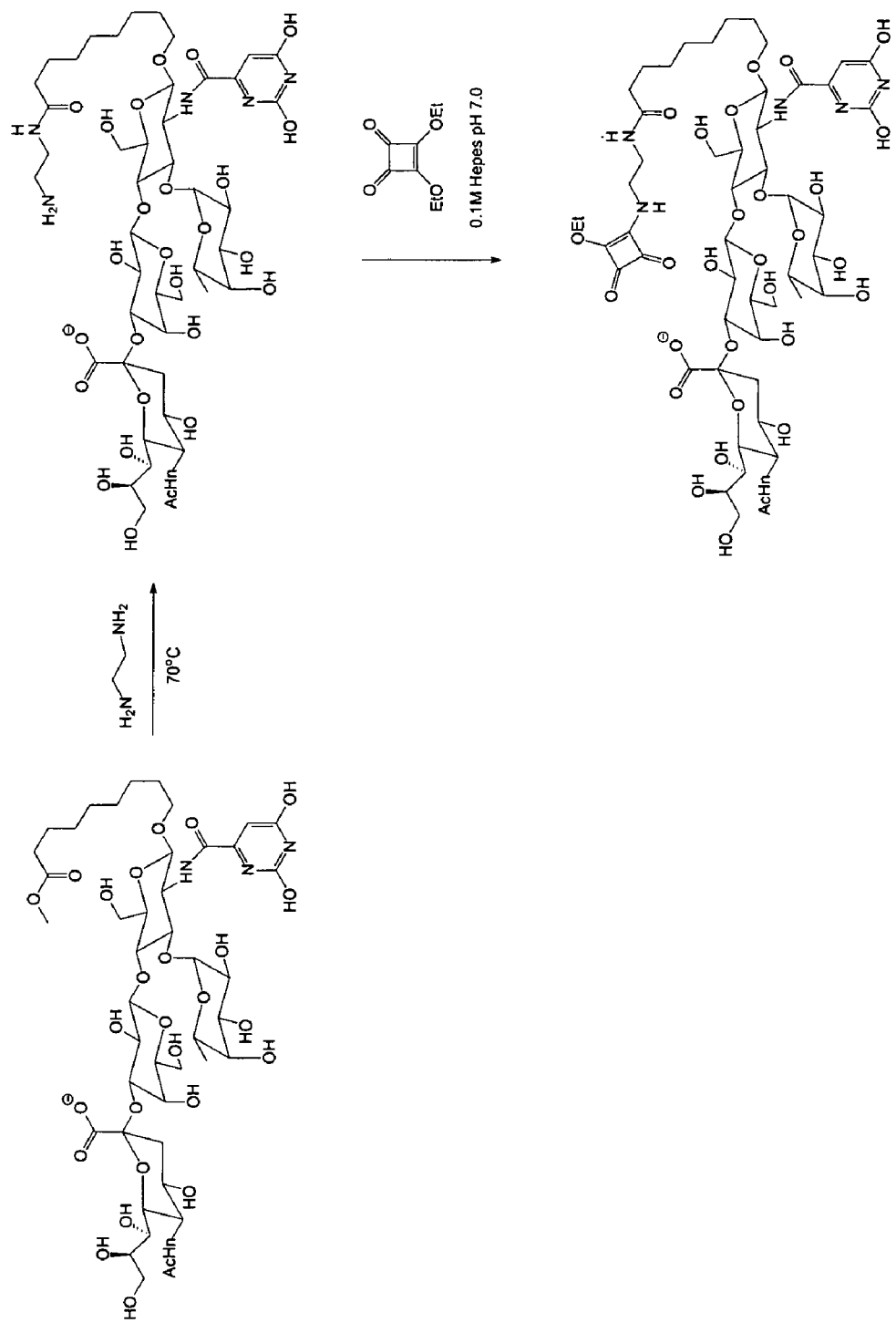
FIG. 9 is a diagram illustrating the coupling of the glycomimetic of FIG. 1 to a squaric acid linker.
Figure 10A:
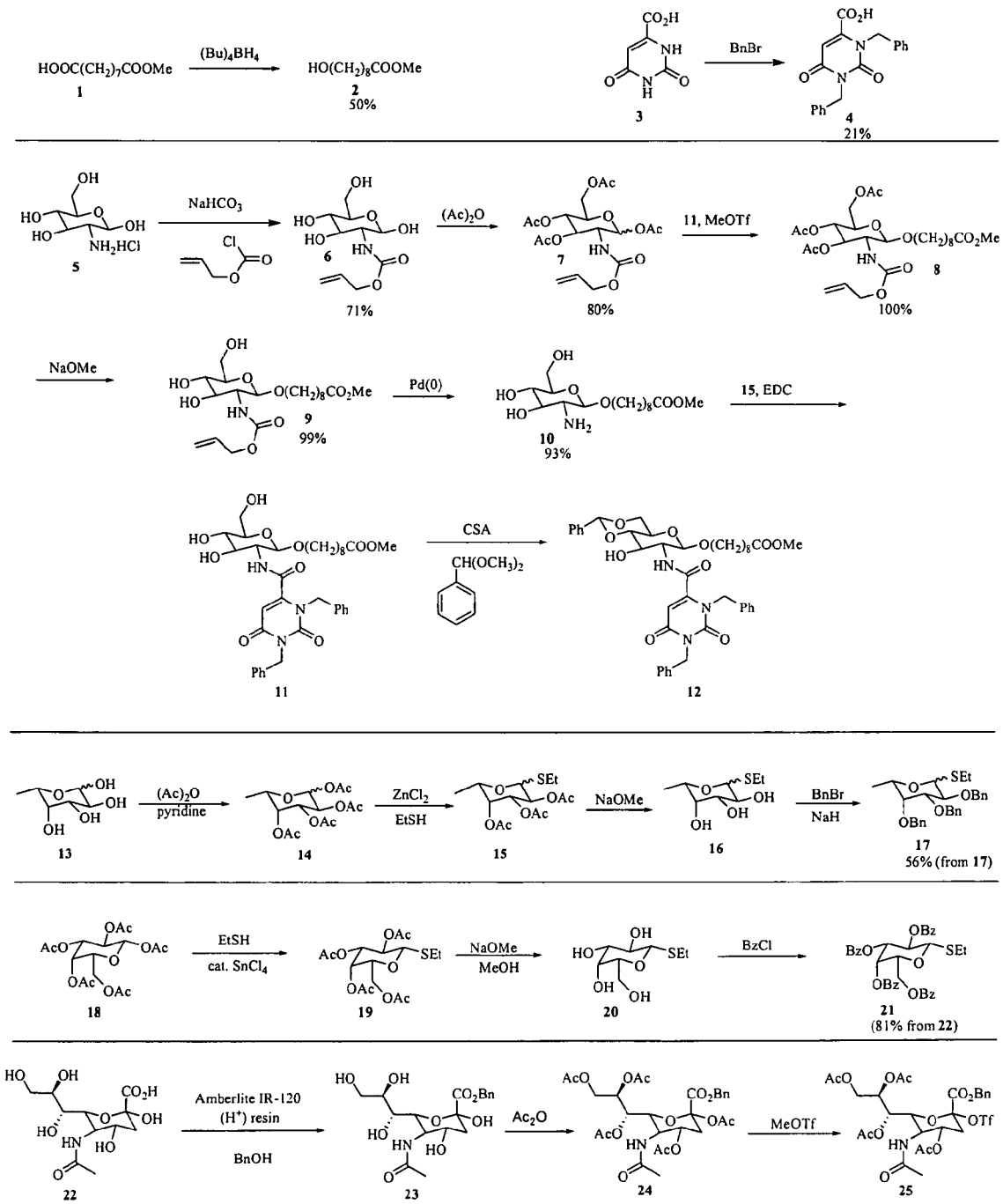
FIGS. 10A-10D show a diagram illustrating the synthesis of a glycomimetic linked to a BASA.
Figure 10B:
Figure 10C:
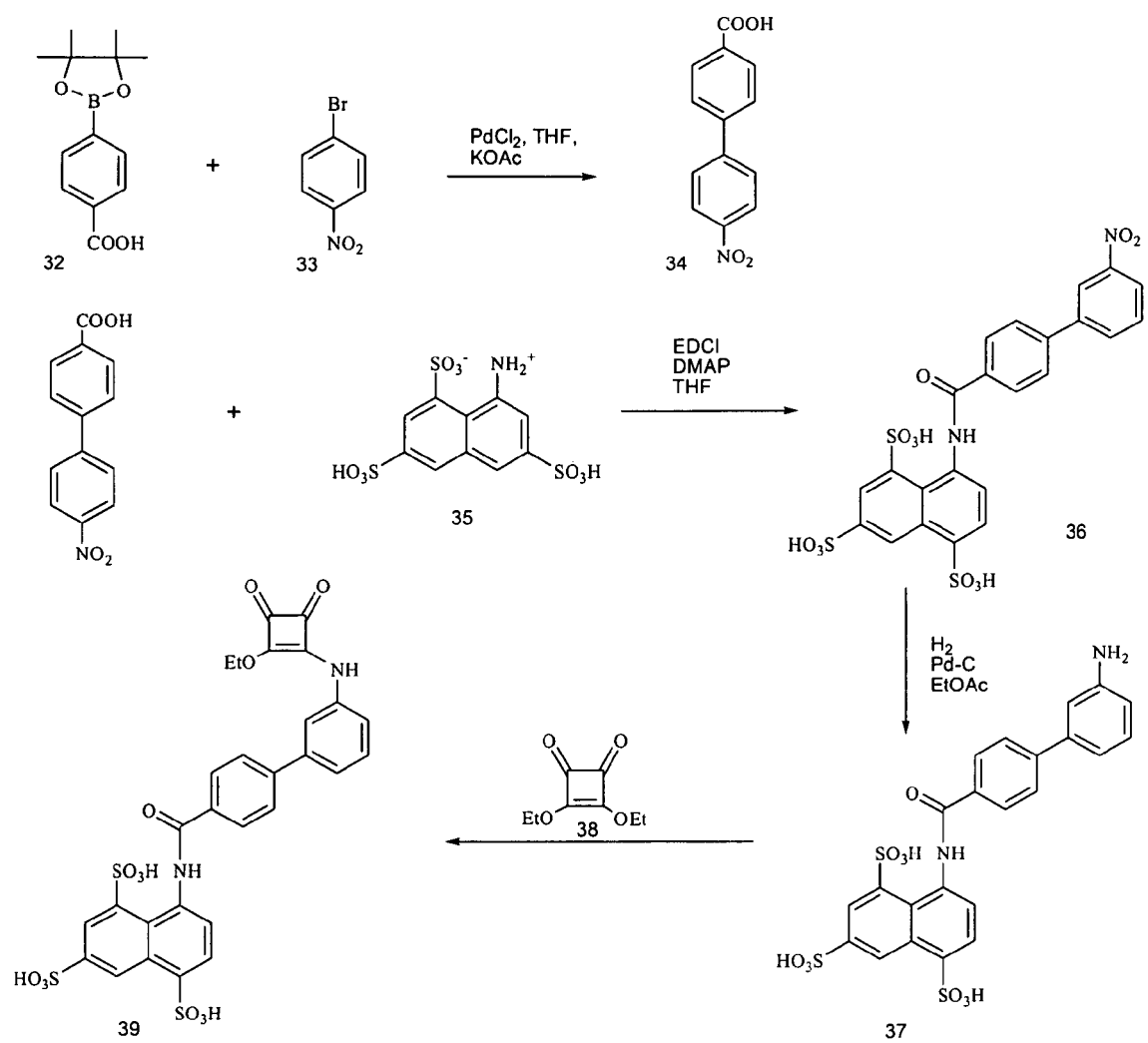
Figure 10D:
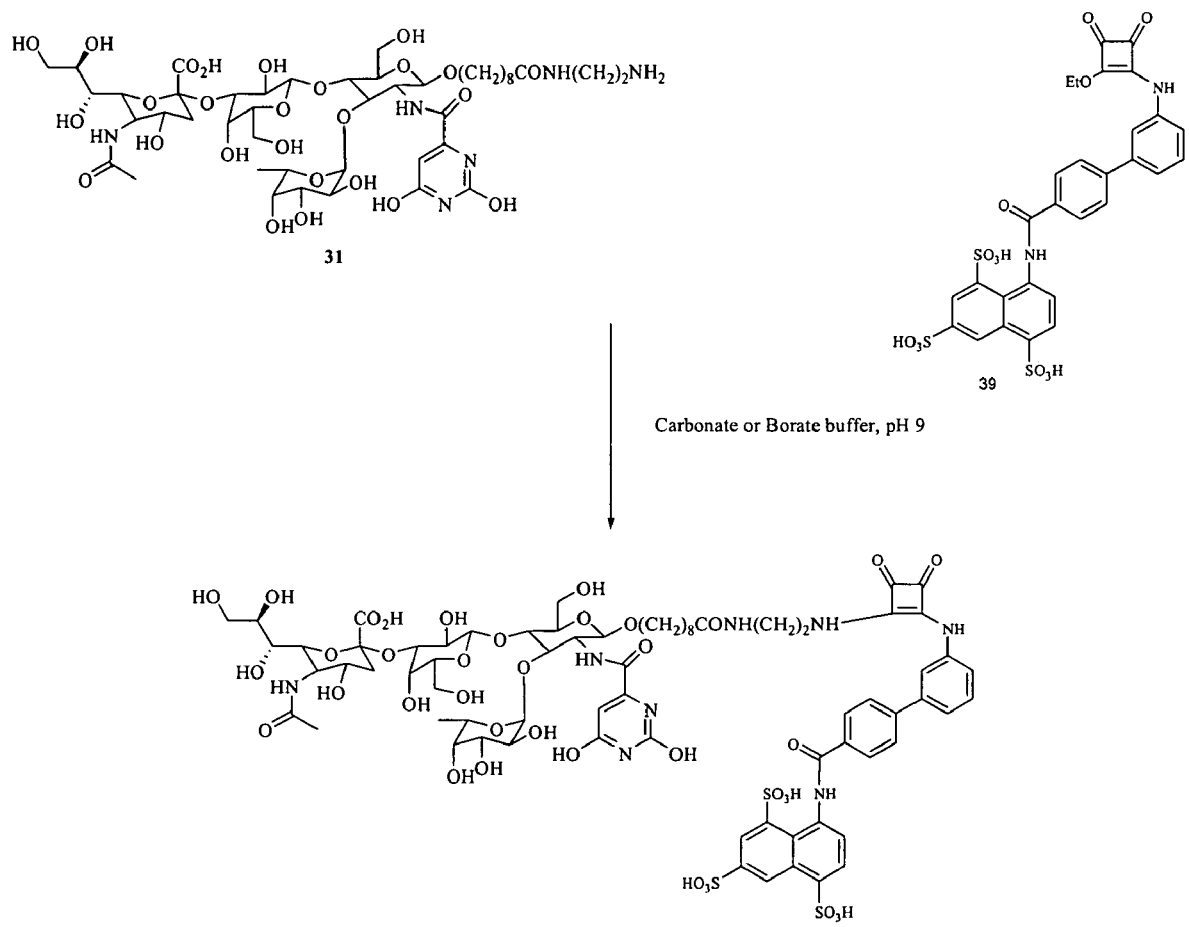

Synthesis of Glycomimetic with Squaric Acid Linker (FIG. 9)

Activated Ester Synthesis

Figure 1:
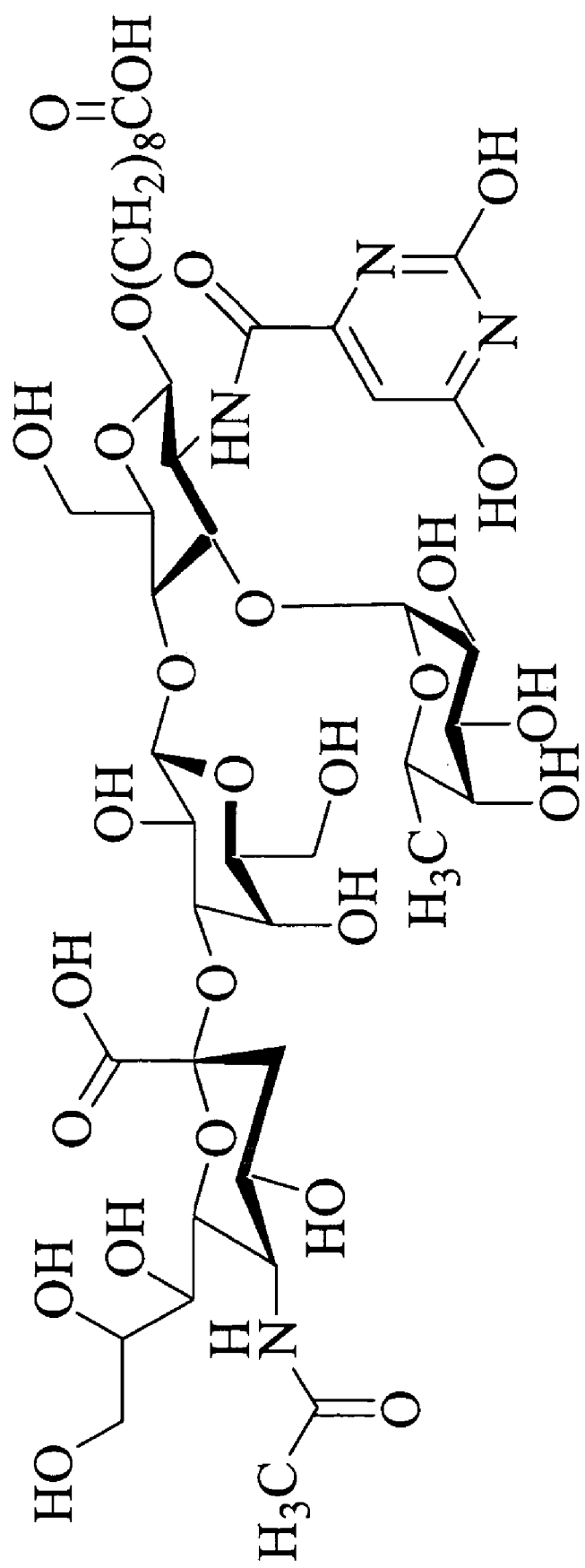
FIG. 1 shows the structure of a particular glycomimetic.
Figure 2:
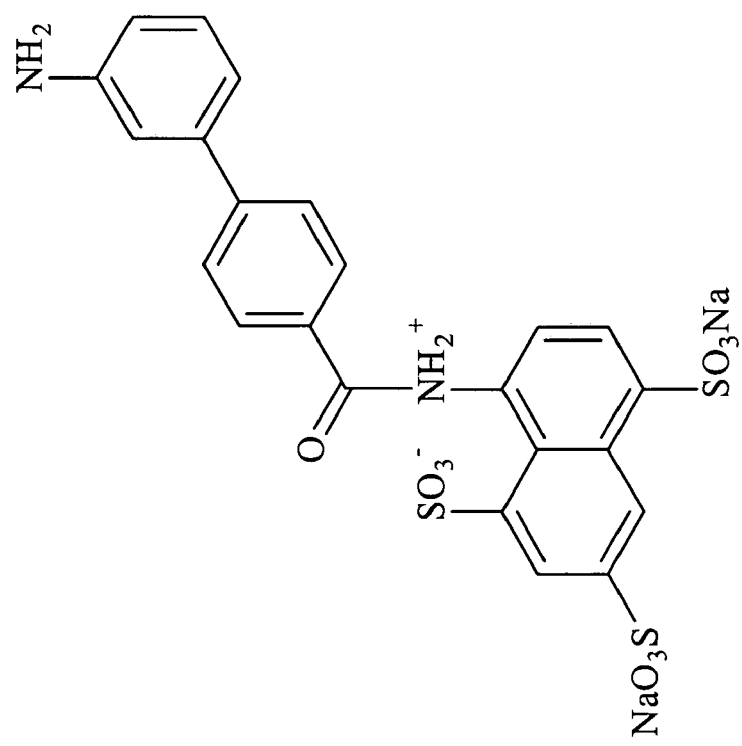
FIG. 2 shows the structure of a particular BASA.
Figure 3:
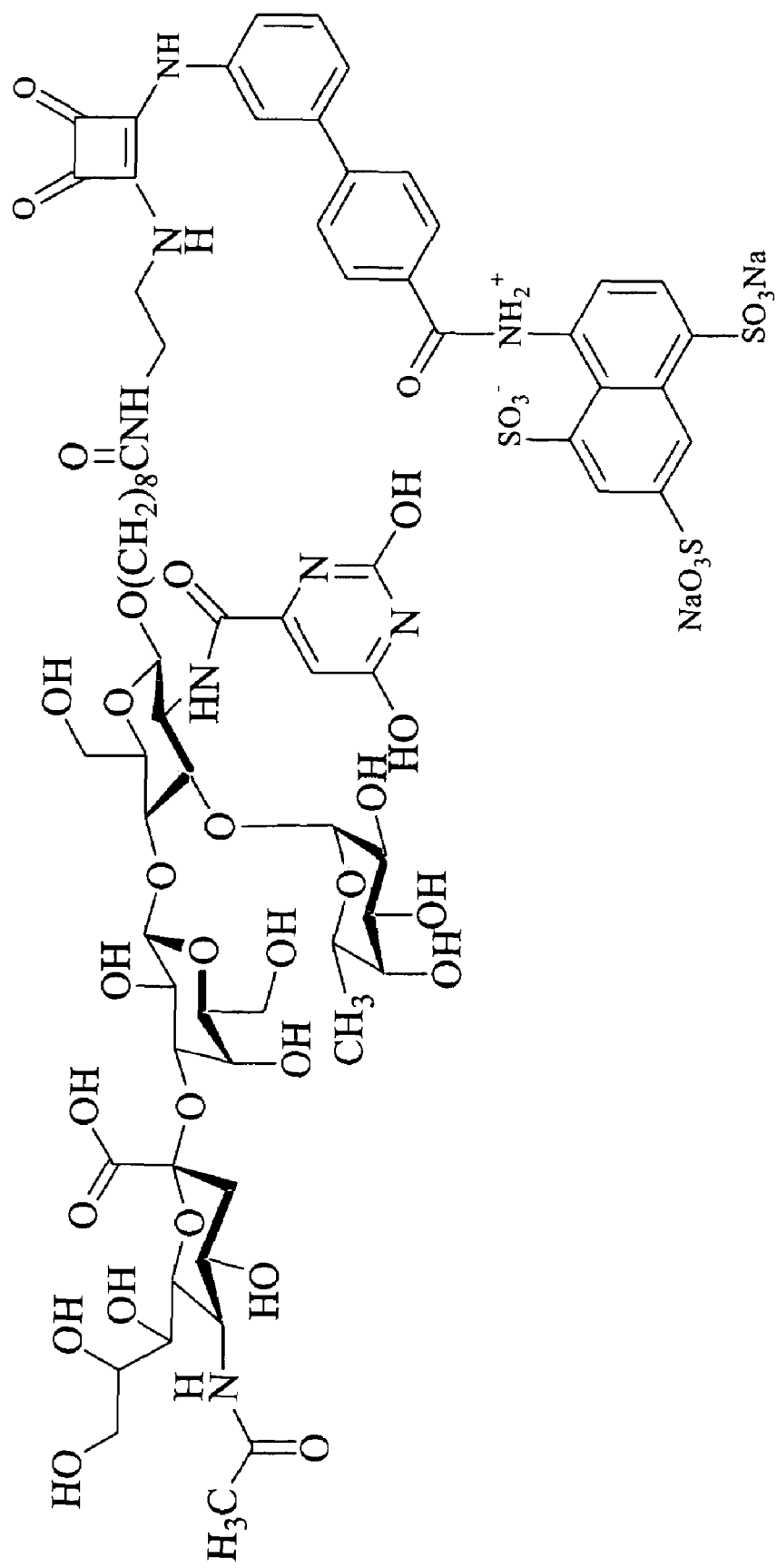
FIG. 3 shows the structure of the glycomimetic of FIG. 1 joined to the BASA of FIG. 2 by a preferred linker.

Compound of FIG. 1 (1.8 µmol, 1 eq) is dissolved in 1,2-diaminoethane (50 µl, XS) with stirring. The solution is heated to 70° C. for 50 hrs under nitrogen. The solution is then evaporated to dryness and the compound is purified by reverse phase chromatography (C18 column, 80/20 $CH_3CN/H_2O$-1% TFA to 50/50 $CH_3CH/H_2O$).

Squarate Ester Formation

The amine (5.40 µmol, 1 eq) is dissolved in 0.1M Hepes buffer of pH 7 and reacted with squaric acid diethyl ester (80 µmol, XS) for 24 hrs. The solution is then washed with $CH_2Cl_2$ and the aqueous layer is collected and evaporated to dryness. The resultant powder is purified by column chromatography (Sephadex-G25, 100% $H_2O$).

Example 3

Synthesis of Glycomimetic-BASA (FIGS. 10A-10D)

Synthesis of Compound 12:

Starting from N-acetyl glucosamine (5, 50 g) compound 12 (50% overall yield) is synthesized following published procedure (*Bioorg. Med. Chem. Lett.* 11, 2001, 923-925; *Carbohydr. Res.* 197, 1990, 75).

Synthesis of Compound 17:

Compound 17 (15 g) is prepared from L-fucose following published procedure (*Carbohydr. Res.* 201, 1990, 15-30).

Synthesis of Compound 21:

Compound 21 is prepared from commercially available β-D-galactose-pentaacetate as described (WO 9701569; *Chem. Astr.* 1997, 126 186312).

Synthesis of Compound 25:

Commercially available N-acetyl neuraminic acid (22, 10 g) is suspended in MeOH—$H_2O$ (60 ml, 9:1), and the pH is adjusted to 8.1 by adding an aqueous solution of cesium carbonate. The solvent is removed, and the residue is repeatedly evaporated with ethanol and then with hexane. The material is dissolved in DMF (65 ml), and benzyl bromide (3.5 ml) is added within 20 min. After the mixture is stirred for 16 h, dichloromethane (100 ml) is added and washed with water (50 ml). The solvent is removed by evaporation and purified by silica gel chromatography to give 23 in 68% yield.

To a solution of compound 23 (7 g) in pyridine (50 ml) is added acetic anhydride (48 ml), and the reaction mixture is stirred at RT for 16 h. Solvent is removed by evaporation and the residue (23a) is dissolved in dry DMF (25 ml). To the mixture is added powdered ammonium carbonate (2 g), and the mixture is stirred for 12 h at 28 degrees centigrade. The mixture is added to an ice-cold solution of 1N HCl in water (50 ml) and dichloromethane (100 ml) is added. After solvent extraction, the organic layer is removed by evaporation and then dried under vacuum for 24 h. The residue is purified by silica gel chromatography to give 24 in 71% yield.

Compound 24 is dissolved in dry dichloromethane, and to this is added 2,6-di-tert-butyl-pyridine (5 g). The solution is cooled to −20 degrees centigrade and trifluoromethanesulfonic anhydride (7 g) is added portionwise in 10 min. The mixture is stirred for 4 h, is diluted with dichloromethane (100 ml), and is added to a solution of potassium hydrogen phosphate (500 ml). The layers are separated, and the organic layer is dried (sodium sulfate) and solvent is removed by evaporation to give 25, which is used without further purification in the preparation of 29.

Synthesis of Compound 26:

To a mixture of compound 12 (10 g) and compound 17 (15 g) in dichloromethane (100 ml) are added molecular sieves (4A, 8 g). After stirring at RT for 1 h, tetraethylammonium bromide (5 g) is added. A solution of bromine (1 g) in dichloromethane (25 ml) is added dropwise during 1 h. The reaction mixture is further stirred for 3 h, filtered through a bed of celite and washed successively with cold water, cold saturated solution of sodium bicarbonate, and cold water. Solvent is removed by evaporation, and the reaction mixture is subjected to silica gel chromatography.

The product is treated with sodium cyanoborohydride in THF and HCl in ether to give compound 26 in 70% overall yield after silica gel chromatography.

Synthesis of Compound 27:

To a mixture of 26 (10 g) and 21 (7 g) in dichloromethane (80 ml) is added N-iodosuccinimide (15 g) and molecular sieves (4A, 8 g), and the mixture is placed in an ice bath. The solution is stirred at 0-5 degree for 30 min, and a solution of triflic acid (0.2 ml) in dichloromethane (25 ml) is added dropwise with stirring during 1 h. Stirring is continued for 2 h, and the mixture is then filtered through a bed of celite and washed successively with cold water, cold saturated solution of sodium bicarbonate, and cold water. Solvent is removed by evaporation, and the mixture is purified by silica gel chromatography to produce 27 in 68% yield.

Synthesis of Compound 28:

Compound 27 (8 g) is treated with 0.05N NaOEt in MeOH (100 ml) for 4 h and, after neutralization with IR120 (hydrogen form) resin, the reaction mixture is filtered. The solvent is removed by evaporation to produce compound 28 in 96% yield.

Synthesis of Compound 29:

Compound 28 (5 g) is treated with dibutyltinoxide (1 g) in MeOH for 4 h under reflux. The solvent is evaporated and then coevaporated with toluene several times. The residue is finally dried under high vacuum for 24 h.

The crude reaction mixture is dissolved in dimethoxyethane (DME, 100 ml) and CsF (1.7 g) is added. The reaction mixture is stirred at RT for 8 h and ethyl acetate (100 ml) is added. The organic layer is washed with water, and the organic solvent is removed by evaporation. The product is purified by silica gel chromatography to produce 29 in 64% yield.

Synthesis of Compound 30:

Compound 29 (2 g) is de-O-acetylated with 0.01N NaOMe in MeOH (100 ml, 1 h), the crude reaction mixture is neutralized with IR120 (hydrogen form) resin, and the solvent is removed by evaporation.

Product from the above reaction is dissolved in dioxane-water (1:1, 50 ml) and 10% PD-C is added. The reaction mixture is stirred vigorously under hydrogen atmosphere for 22 h, filtered through a bed of celite, and the solvent is removed by evaporation. Silica gel chromatography of the resulting syrup produced 30 in 77% yield.

Synthesis of Compound 31:

Compound 30 (500 mg) is treated with ethylenediamine at 70 degrees centigrade for 4 h. Solvent is removed by evaporation and the syrupy residue is purified by silica gel chromatography to produce compound 31 in 77% yield.

Synthesis of Compound 39:

Commercially available compound 32 (4-(4,4,5,5-tetramethyl-[1,3,2]dioxaborolan-2-yl)-benzoic acid, 1 eq) and KOAc (3 eq) are placed in THF (25 ml). To the resulting slurry is added $PdCl_2$ and p-bromonitrobenzene (33, 1.2 eq) with stirring, and the mixture is gently heated to 80 degrees centigrade. After 6 h, the reaction mixture is evaporated to dryness, dissolved in dichloromethane (30 ml) and washed with distilled water and a saturated solution of sodium bicarbonate. The resulting biphenyl compound 34 is taken directly to the next step.

Compound 34 (1 eq), dimethylaminopyridine (catalytic amount, one crystal), and EDCI (1.05 eq) are dissolved in DMF or THF (20 ml) and allowed to react at RT for 10 min. Commercially available compound 35 (8-aminonaphthalene-1,3,5-trisulfonic acid) is added to the reaction mixture with stirring, and the reaction is allowed to proceed at RT under nitrogen for 48 h. The reaction mixture is then evaporated to dryness and purified by reverse phase chromatography to yield compound 36.

To a solution of compound 36 in EtOAc is added PD-C, and the reaction mixture is stirred for 2 h under a hydrogen atmosphere. The reaction mixture is filtered through a bed of celite and evaporated to dryness to yield compound 37.

To a solution of compound 37 in phosphate buffer (pH 7.1) is added squaric acid (38), and the reaction mixture is stirred for 4 h at RT. It is then purified by reverse phase hplc to yield compound 39.

Synthesis of Compound 40:

Compound 31 (0.2 g) is dissolved in carbonate buffer (2 ml, pH 8.8), and compound 39 (0.4 g) is added. The reaction mixture is stirred at RT for 24 h. Another batch (0.2 g) of compound 39 is added, and stirring is continued for 20 h at RT. Solvent is removed by evaporation, and the mixture is purified by chromatography on Sephadex G-25 in 5 mM ammonium bicarbonate to yield compound 40.

Example 4

Figure 11:
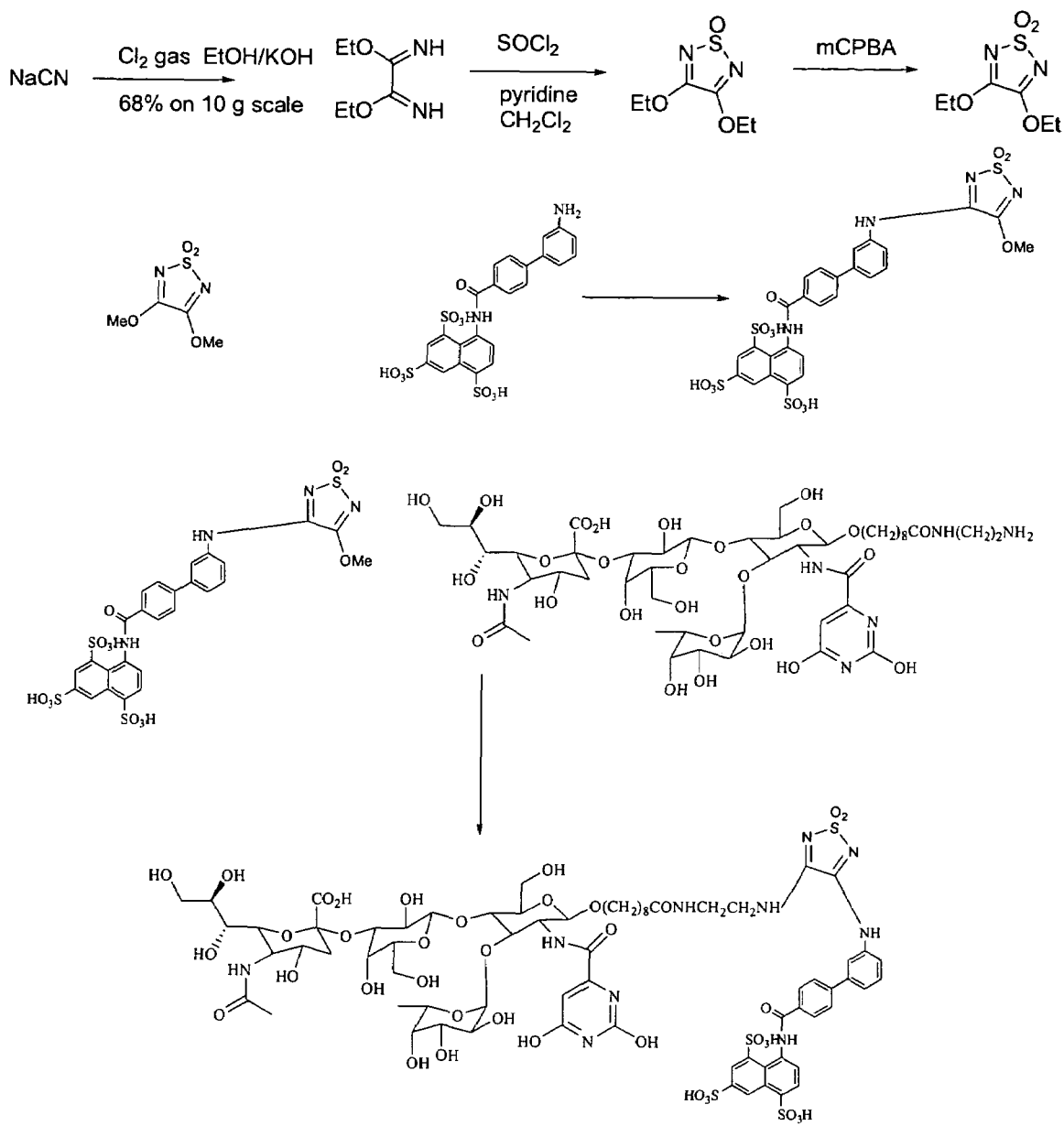
FIG. 11 is a diagram illustrating the synthesis of a glycomimetic linked to a BASA.

Synthesis of Glycomimetic-BASA (FIG. 11)

SYNTHESIS OF
3,4-DIETHOXY-DITHIADIAZOLE,
3,4-DIETHOXY-DITHIADIAZOLE-1-OXIDE,
AND
3,4-DIETHOXY-DITHIADIAZOLE-1,1-DIOXIDE

Synthesis of the above compounds was performed as described previously (SACS 1996, 118, 330-338; JACS 1982, 104, 1375; JOC, 1975, 40, 2749).

Synthesis of Intermediate I

The BASA of Example 1 is added to a solution of 3,4-diethoxy-dithidiazole-1,1-dioxide in ethanol at room temperature and stirred for 5 h. Ethanol was evaporated off and the crude mixture is purified to give intermediate I.

Conjugation Between Intermediate I and Compound 31

Intermediate I is reacted with compound 31 of Example 3 in ethanol to give the glycomimetic-BASA which is purified by sephadex G-25 column.

Example 5

Figure 12:
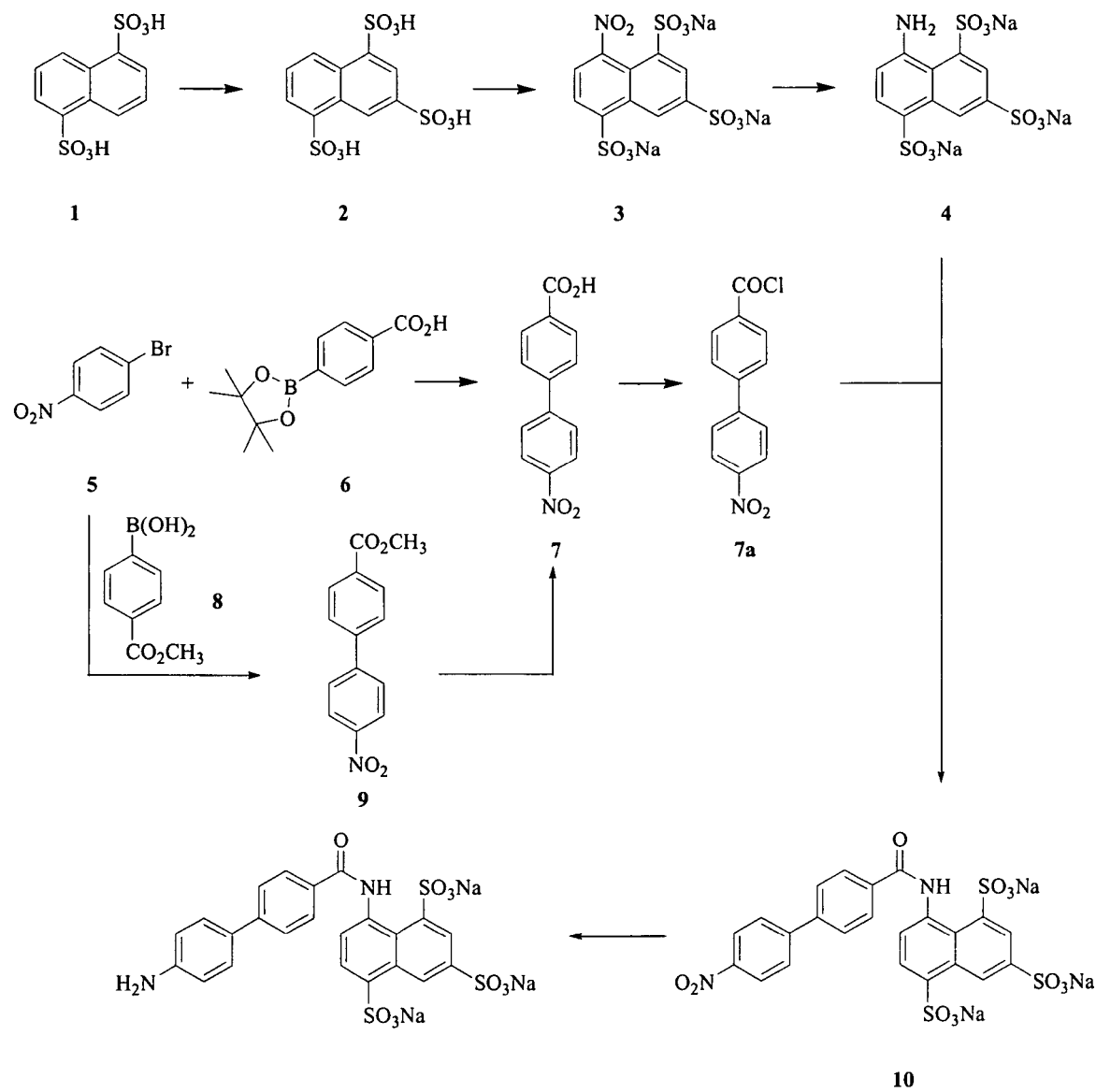
FIG. 12 is a diagram illustrating the synthesis of a particular BASA.

Preparation of a BASA (FIG. 12)

Synthesis of Compound 4

Nitration of commercially available 2 (1 g) was according to the procedure described in the literature (U.S. Pat. No. 4,534,905; Allison, F. et al. *Helv. Chim. Acta* 1952, 4, 2139). The crude product 3 was dissolved in water (40 mL) and 10% Pd/C (0.3 g) added. The mixture was hydrogenated (~45 psi) at room temperature for 48 h. The catalyst was filtered through Celite and the filter bed was washed with water. The filtrate was concentrated under vacuum to afford a pink solid. After removal of the catalyst, the filtrate was concentrated to 15 mL and an equal volume of ethanol was added. The precipitate was collected by filtration to give compound 4 with very little impurity.

Synthesis of Compound 7A

A solution of 5 (5 g) and 8 (4.45 g, 24.7 mmol), and $K_2CO_3$ (2 M in $H_2O$, 24.7 mL, 49.4 mmol) in 10:1 toluene/ethanol (70 mL) was treated with $Pd(PPh_3)_4$ (1.43 g, 1.24 mmol) and the mixture was refluxed for 20 h. After work up, recrystallization of the crude product in EtOH and chromatographic purification of the recrystallization filtrate afforded compound 9 (2.9 g, 46%, >90% HPLC) and 2.2 g of recovered 5. The product was characterized by $^1H$ NMR.

A mixture of 9 (2.9 g, 11.3 mmol) and $LiOH.H_2O$ (1.43 g, 34.1 mmol) in 1:1 $THF/H_2O$ (250 mL) was stirred at RT for 21 h. The reaction afforded 7 (2.58 g, 94%, >90% HPLC) after work up. The product was characterized by $^1H$ NMR.

DMF (20 µL) was added to a suspension of 7 (500 mg, 1.94 mmol), $SOCl_2$ (0.23 mL, 3.10 mmol) and toluene (3 mL) and then heated to 80° C. After 20 h, the reaction was worked up to afford the acid chloride (640 mg). The product was characterized by IR and $^1H$ NMR.

Synthesis of Compound 10

To a solution of amine 4 (268 mg, 0.641 mmol) in $H_2O$ (2 mL) and dioxane (18 mL) was added a solution of 7a (273 mg, 0.99 mmol) in dioxane (16 mL) dropwise over 30 min. The pH of the reaction mixture was adjusted to 8.5 with 0.25 M NaOH as the addition progressed. The reaction was stirred at room temperature for 2.5 h after the addition. Purification by column chromatography (methanol/toluene 1:1) followed by prep. TLC (methanol/toluene 1:1) afforded 50 mg of compound 10, which was characterized by $^1H$ NMR and MS.

Hydrogenation of Compound 10

A suspension of 10 (30 mg, 0.049 mmol) and 10% Pd on carbon (50 mg) in $H_2O$ (20 mL) was hydrogenated (55 psi) at room temperature for 4 h to yield the BASA.

Example 6

Figure 13:
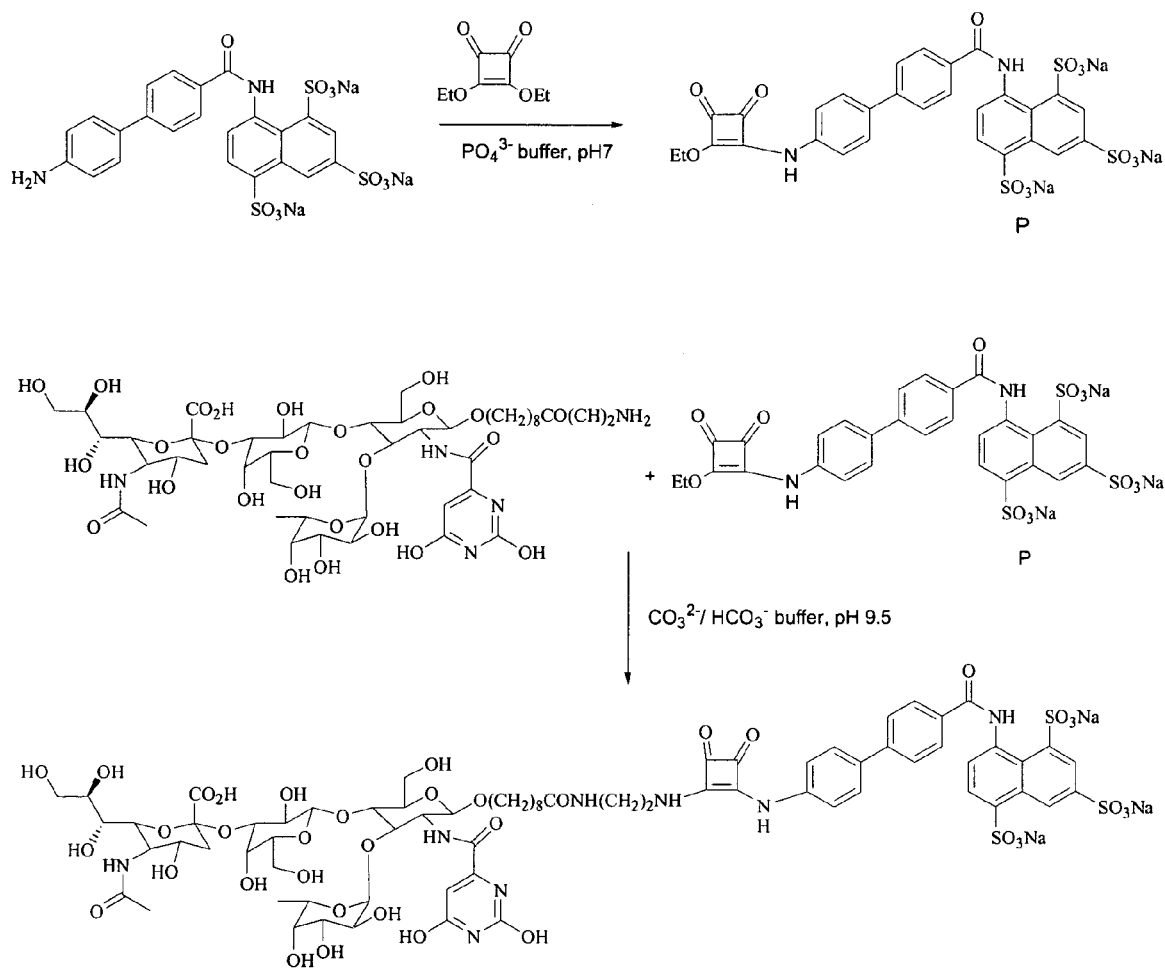
FIG. 13 is a diagram illustrating the synthesis of a glycomimetic linked to a BASA.

Synthesis of Glycomimetic-BASA (FIG. 13)

Synthesis of Intermediate P

The BASA of Example 5 was reacted with diethyl squarate (5 mg) in phosphate buffer at pH 7 and then purified by preparative hplc to give intermediate P.

Condensation Between Intermediate P and Compound 31

To a solution of intermediate P (15 mg) in carbonate/bicarbonate buffer (pH 9.5, 1.5 ml) was added compound 31 of Example 3 (10 mg) and the reaction mixture was stirred at room temperature for 16 h. The reaction mixture was then applied to column of sephadex G-25 and the column was eluted with 5 mM ammoniumbicarbonate solution. The fractions correspond to the product was collected and lyophilized to yield the glycomimetic-BASA (12 mg).

Example 7

Synthesis of Glycomimetic-BASA (FIG. 14)

To a solution of the BASA of Example 5 in 0.2M sodium bicarbonate solution was added a solution of thiphosgene in chloroform. The mixture was stirred vigorously for 1 h and the aqueous layer was collected to afford intermediate J.

To the above mixture was added a solution of compound 31 of Example 3 in carbonate/bicarbonate buffer (pH 10) and the mixture was stirred for 16 h at room temperature. The crude product was purified by gel filtration to give the glycomimetic-BASA.

Example 8

Assay for E-Selectin Antagonist Activity (FIGS. 15A-15B)

Wells of a microtiter plate (plate 1) are coated with E-selectin/hIg chimera (GlycoTech Corp., Rockville, Md.) by incubation for 2 hr at 37° C. After washing the plate 5 times with 50 mM Tris HCl, 150 mM NaCl, 2 mM $CaCl_2$, pH 7.4 (Tris-Ca), 100 µl of 1% BSA in Tris-Ca/Stabilcoat (SurModics, Eden Prairie, Minn.) (1:1, v/v) are added to each well to block non-specific binding. Test compounds are serially diluted in a second low-binding, round bottomed plate (plate 2) in Tris-Ca (60 µl/well). Preformed conjugates of SLea-PAA-biotin (GlycoTech Corp., Rockville, Md.) mixed with Streptavidin-HRP (Sigma, St. Louis, Mo.) are added to each well of plate 2 (60 μl/well of 1 μg/ml). Plate 1 is washed several times with Tris-Ca and 100 μl/well are transferred from plate 2 to plate 1. After incubation at room temperature for exactly 2 hours the plate is washed and 100 μl/well of TMB reagent (KPL labs, Gaithersburg, Md.) is added to each well. After incubation for 3 minutes at room temperature, the reaction is stopped by adding 100 μl/well of 1M $H_3PO_4$ and the absorbance of light at 450 nm is determined by a microtiter plate reader.

Example 9

Assay for P-Selectin Antagonist Activity (FIGS. 16A-16B)

The neoglycoprotein, sialylLe$^a$-HSA (Isosep AB, Sweden) is coated onto wells of a microtiter plate (plate 1) and the wells are then blocked by the addition of 2% bovine serum albumin (BSA) diluted in Dulbecco's phosphate-buffered saline (DPBS). In a second microtiter plate (plate 2), test antagonists are serially diluted in 1% BSA in DPBS. After blocking, plate 1 is washed and the contents of plate 2 are transferred to plate 1. Pselectin/hIg recombinant chimeric protein (GlycoTech Corp., Rockville, Md.) is further added to each well in plate 1 and the binding process is allowed to incubate for 2 hours at room temperature. Plate 1 is then washed with DPBS and peroxidase-labelled goat anti-human Ig(γ) (KPL Labs, Gaithersburg, Md.) at 1 μg/ml is added to each well. After incubation at room temperature for 1 hour, the plate is washed with DBPS and then TMB substrate (KPL Labs) is added to each well. After 5 minutes, the reaction is stopped by the addition of 1M $H_3PO_4$. Absorbance of light at 450 nm is then determined using a microtiter plate reader.

Example 10

Assay for Effect of a Compound on Cell Rolling in Established Inflammation

Inflammation is induced in normal Swiss Albino mice by intraperitoneal injection of IL-1β (10 ng). After 4 hours, the established inflammatory response is treated with test compounds by intravenous injection. Vehicle is the negative control containing no test compound and mAbs(3) is the positive control containing a cocktail of antibodies to all three selectins (E, 10E9; L, Mel-14; P, RB40.34). Test compound (FIG. 6) is administered (n=3) at 50 mg/kg. Rolling of cells on the endothelium is determined by intravital microscopy of the post-capillary venules of the mouse mesentery. Results are shown in FIG. 17. Effects of treatment with vehicle (◆ monoclonal antibodies ■ and test compound ▲ on cell rolling is monitored for 30 minutes immediately after administration.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound or physiologically acceptable salt thereof, having the formula:

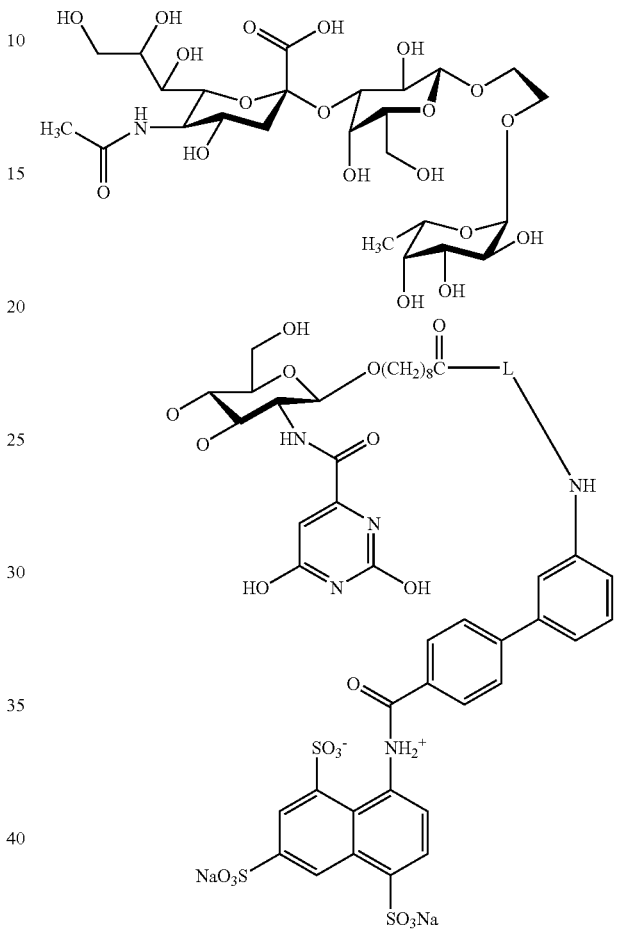

wherein L is a linker.

2. The compound or physiologically acceptable salt thereof of claim 1 wherein L is

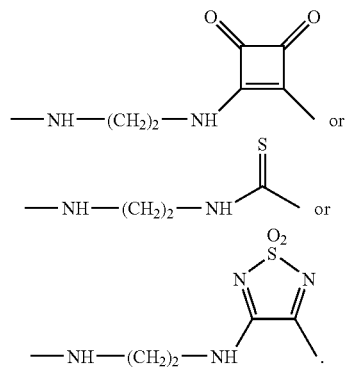

3. A compound or physiologically acceptable salt thereof, having the formula:

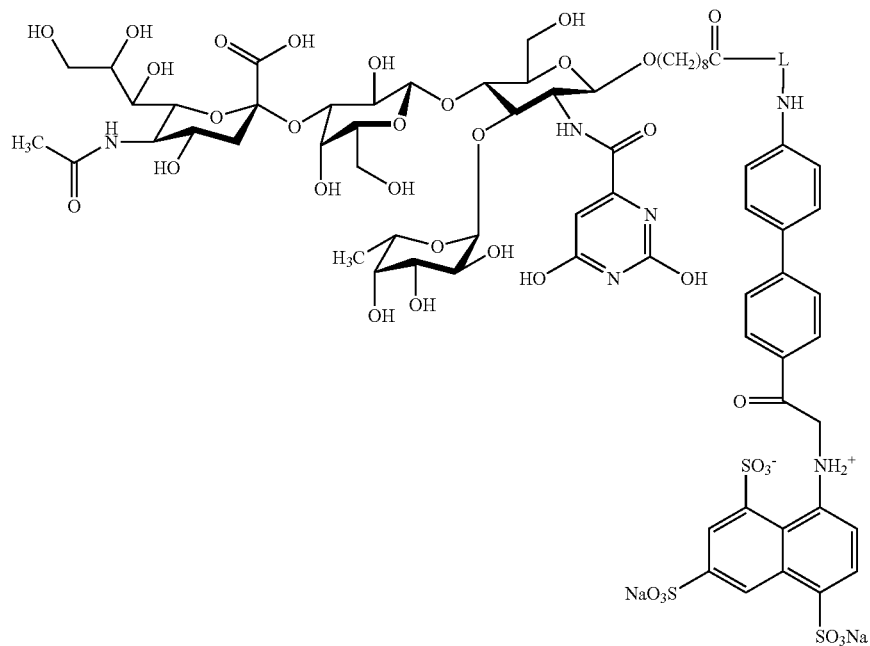
wherein L is a linker.
4. The compound or physiologically acceptable salt thereof of claim 3 wherein L is
-continued
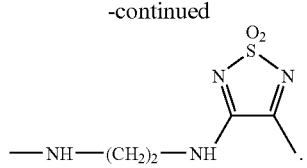
5. A composition comprising a compound or physiologically acceptable salt thereof according to any one of claims 1-4 in combination with a pharmaceutically acceptable carrier or diluent.
* * * * *

UNITED STATES PATENT AND TRADEMARK OFFICE
CERTIFICATE OF CORRECTION

PATENT NO. : 7,361,644 B2
APPLICATION NO. : 10/992480
DATED : April 22, 2008
INVENTOR(S) : John L. Magnani et al.

Page 1 of 2

It is certified that error appears in the above-identified patent and that said Letters Patent is hereby corrected as shown below:

Column 18

Lines 5-45   " 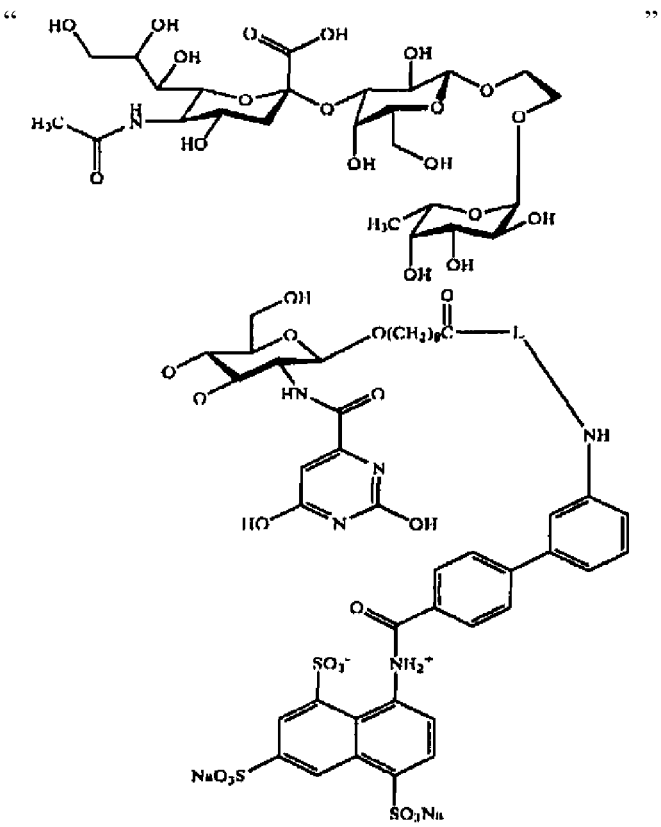 "

UNITED STATES PATENT AND TRADEMARK OFFICE
CERTIFICATE OF CORRECTION

PATENT NO. : 7,361,644 B2
APPLICATION NO. : 10/992480
DATED : April 22, 2008
INVENTOR(S) : John L. Magnani et al.

It is certified that error appears in the above-identified patent and that said Letters Patent is hereby corrected as shown below:

should read as

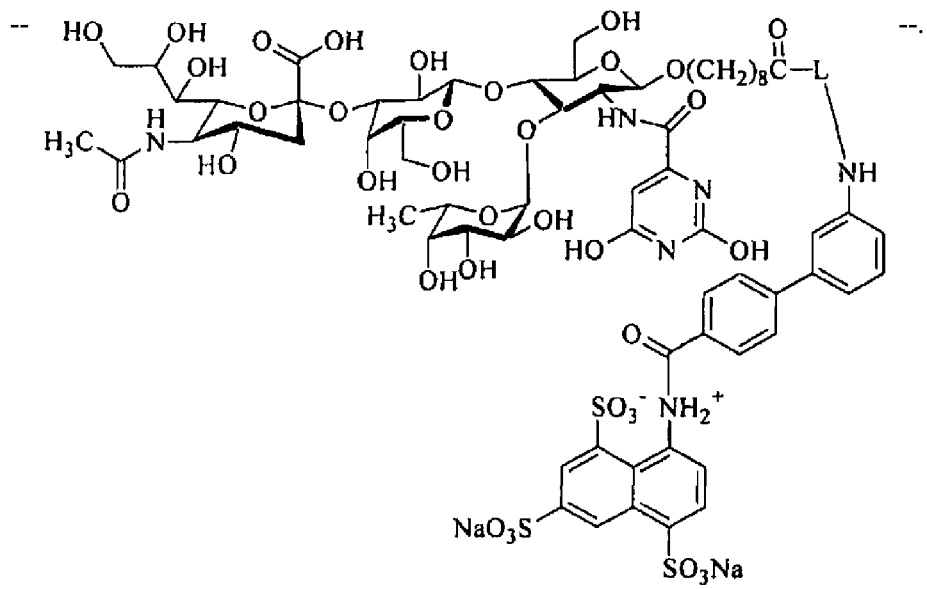

Signed and Sealed this

Thirtieth Day of December, 2008

JON W. DUDAS
*Director of the United States Patent and Trademark Office*

UNITED STATES PATENT AND TRADEMARK OFFICE
CERTIFICATE OF CORRECTION

Page 1 of 2

PATENT NO. : 7,361,644 B2
APPLICATION NO. : 10/992480
DATED : April 22, 2008
INVENTOR(S) : John L. Magnani et al.

It is certified that error appears in the above-identified patent and that said Letters Patent is hereby corrected as shown below:

Column 19, Lines 1-28:

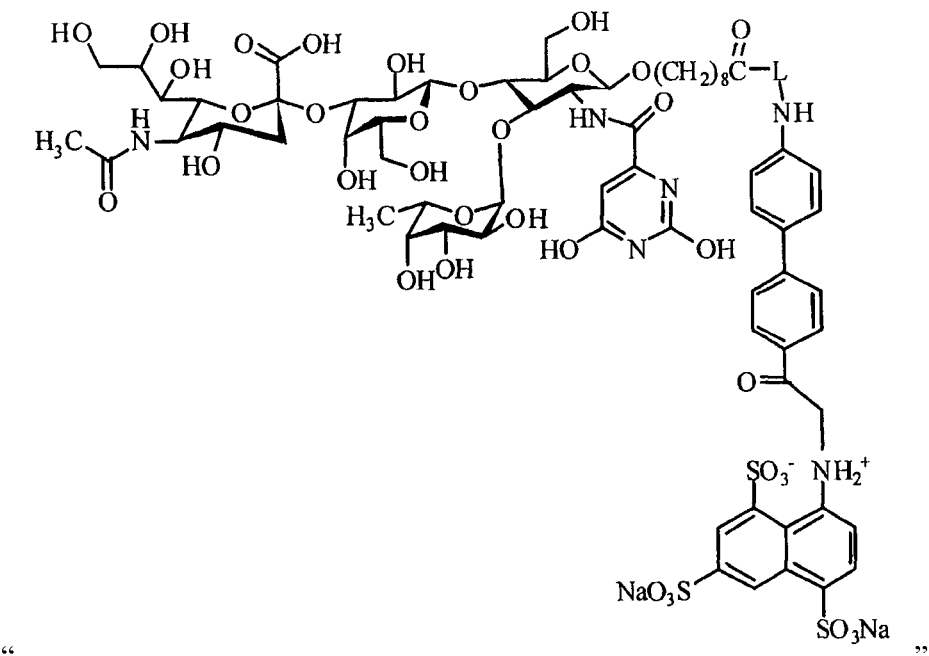

"                                                                                            "

Signed and Sealed this
Twentieth Day of November, 2012

David J. Kappos
*Director of the United States Patent and Trademark Office*

CERTIFICATE OF CORRECTION (continued)
U.S. Pat. No. 7,361,644 B2 should read,

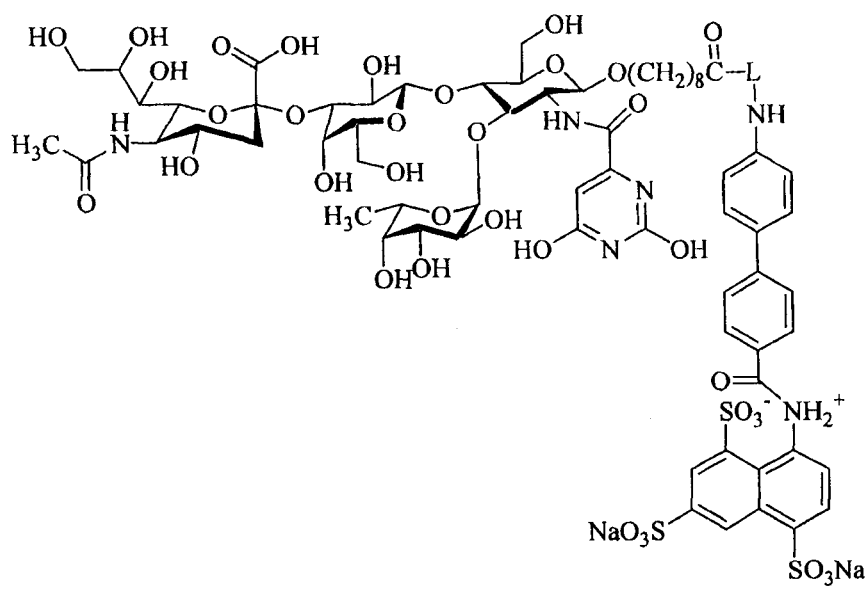

-- --.